United States Patent [19]

Thomas et al.

[11] Patent Number: 4,818,103

[45] Date of Patent: Apr. 4, 1989

[54] FLOW CYTOMETRY

[75] Inventors: Richard A. Thomas, Miami, Fla.; Jerry T. Thornthwaite, Johnson City, Tenn.; Ross W. Eggelston, Miami, Fla.

[73] Assignee: Ratcom, Miami, Fla.

[21] Appl. No.: 5,280

[22] Filed: Jan. 20, 1987

Related U.S. Application Data

[63] Continuation of Ser. No. 648,356, Sep. 7, 1984, Pat. No. 4,673,288, which is a continuation of Ser. No. 263,882, May 15, 1981.

[51] Int. Cl.$^4$ ............... G01N 21/05; G01N 27/08
[52] U.S. Cl. ........................ 356/72; 324/71.4; 356/246
[58] Field of Search ........... 356/39, 72, 73, 246; 648/356; 324/71.4

[56] References Cited

U.S. PATENT DOCUMENTS

| | | | |
|---|---|---|---|
| 3,497,690 | 2/1970 | Wheeless, Jr. et al. | 356/71 |
| 3,628,140 | 12/1971 | Hogg et al. | 324/71.1 |
| 3,710,933 | 1/1973 | Fulwyler et al. | 356/73 X |
| 3,739,258 | 6/1973 | Karuhn et al. | 324/71.1 |
| 3,810,010 | 5/1974 | Reinhard | 324/72 |
| 3,924,951 | 12/1975 | Dittrich | 356/246 X |
| 4,673,288 | 6/1987 | Thomas et al. | 324/71.4 X |

OTHER PUBLICATIONS

"Uniform Lateral Orientation, Caused by Flow Forces of Flat Particles in Flow-Through Systems", *the Jour. of Histochemistry & Cytochemistry*, vol. 25, #7, pp. 774-780, 1977.

"Combined Optical Telectronic Analysis of Cells with the AMAC Transducers"-R. A. Thomas et al.

*Primary Examiner*—Vincent P. McGraw
*Attorney, Agent, or Firm*—Irell & Manella

[57] ABSTRACT

A flow cytometer has an aperture in which an inlet chamber and/or an outlet chamber have predetermined geometric relationships with respect to the aperture for decreasing electronic edge effects and increasing the sensitivity of electronic particle volume measurements. In one embodiment, the aperture is triangular and is formed by assembling a plurality of truncated pyramids with their truncated surfaces defining aperture walls. At least one of the elements forming the aperture walls is either part of a lens systems or a transparent cover plate so that simultaneous optical and electronic cell volume measurements can be performed. In one embodiment, a piezoelectric transducer is provided to sonically clear any aperture clogging.

6 Claims, 17 Drawing Sheets

CURRENT FLUX DENSITY

UNIFORM DENSITY

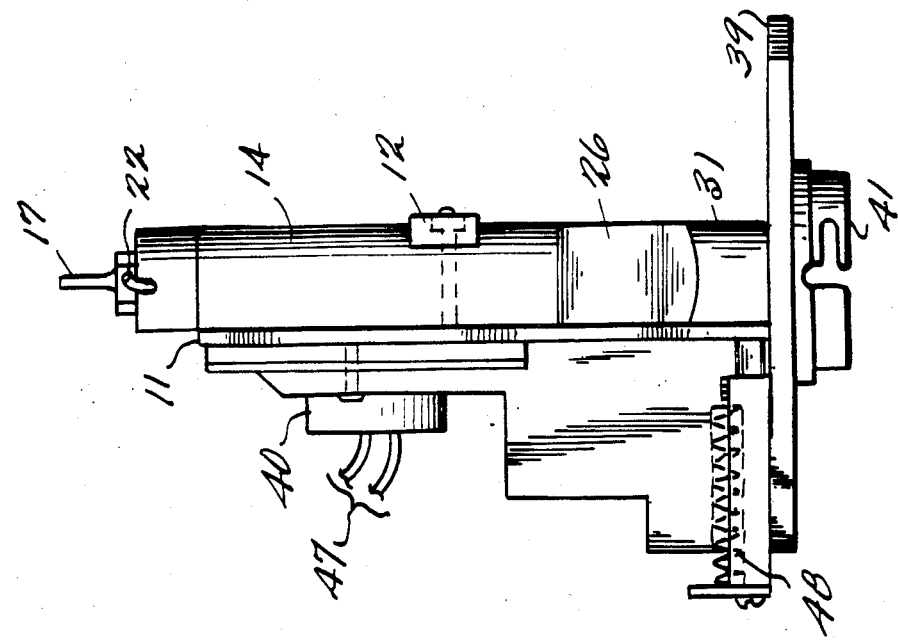
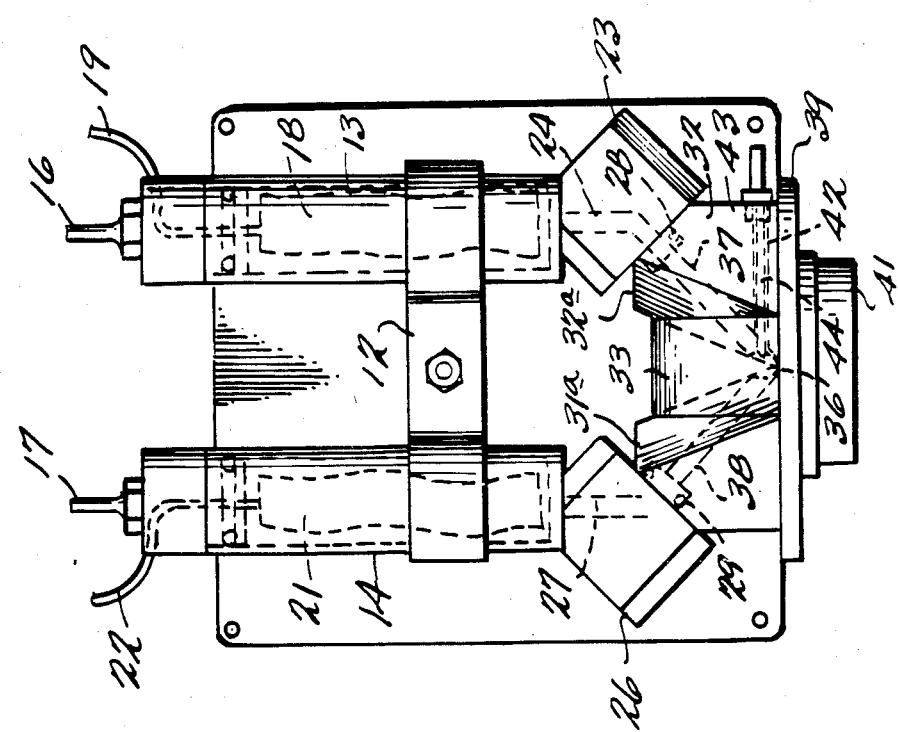

FIG. 10
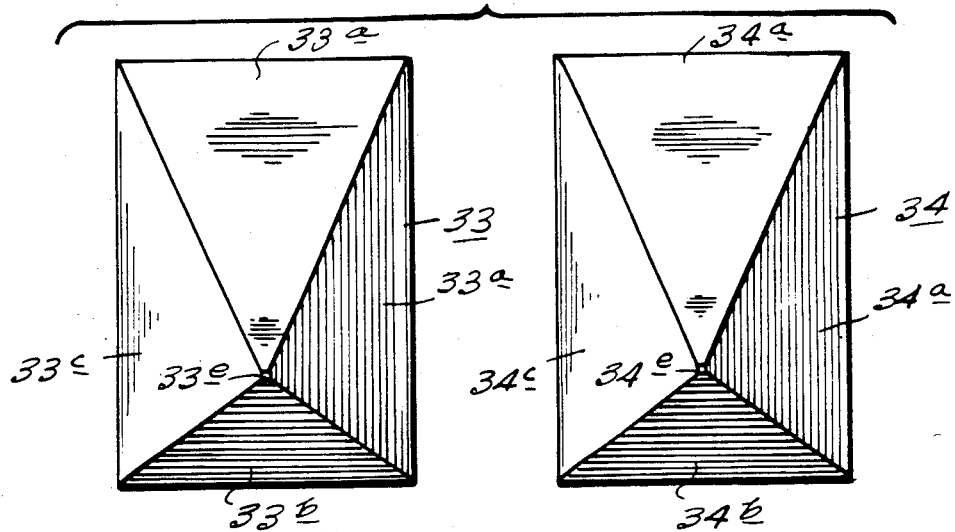
FIG. 11
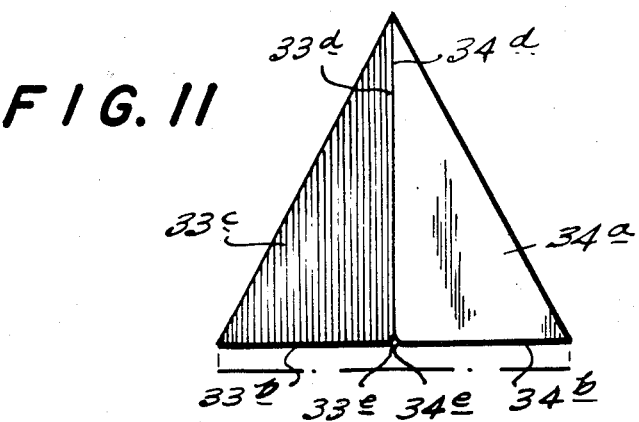
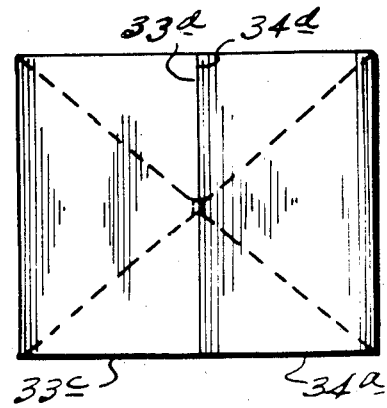
FIG. 12

(a)    (b)

FLOW CYTOMETRY

This is a continuation of application Ser. No. 648,356, filed Sept. 7, 1984 now U.S. Pat. No. 4,673,288 which was a continuation of application Ser. No. 263,882 filed May 15, 1981, now abandoned.

BACKGROUND OF THE INVENTION

This invention pertains to flow cytometry, and more particularly pertains to a flow cytometer in which simultaneous optical measurements and electronic particle volume measurement can be made.

The history of flow particle analyzers is divided into two main lines of development, these being optical on the one hand and electronic on the other hand. Further, there have recently been various proposals for combining the optical and electronic techniques. A basic text covering the history of the entire field is FLOW CYTOMETRY AND SORTING: Melamed, Mullaney, Mendelson, et al, John Wiley & Sons; New York; 1979. In order to facilitate understanding the features and advantages of the present invention and by way of a background to it, brief summaries of the development of the optical, electronic and combined techniques are set forth hereafter.

Optical Flow Particle Analyzers

Optical flow cytometry has been in development over the last 25 years. These systems initially were used to count cells or particles in accordance with the change in absorbence of an illuminating light as the cells were passed through a glass capillary tube in the measurement path of a photoelectric measuring device. Later improvements included the provision of laminar sheath flow of the particles or cells past the observing area. In this, a suspension of the cells or particles under investigation is injected into a faster flowing stream of fluid. This faster flowing fluid provided a sheath around the particles, producing laminar flow. The laminar flow addition was important because it allowed use of a large diameter flow stream, thus minimizing clogging and precisely centering sample streams of particles or cells in an analysis volume.

The literature concerning developments related to laminar flow and hydrodynamic focusing techniques is discussed in the FLOW CYTOMETERY AND SORTING text. Patents related to various aspects of this subject include U.S. Pat. Nos. 3,299,354; 3,661,460; 3,738,759; 3,740,665; 3,810,010; 3,871,770; 3,984,307; 4,140,966; 4,162,282; and 4,237,416;

Besides absorption optical measures, both light scatter and fluorescence are techniques that have also been used to analyze cells or particles. In this connection, see the extensive discussion of these techniques and the bibliographies contained in the FLOW CYTOMETRY AND SORTING text discussed above. Patents related to light scatter techniques include U.S. Pat. Nos. 3,614,231; 3,646,352; 3,669,542; 3,705,771; 3,785,735; 3,786,261; 3,873,204; 3,960,449; 4,053,229; 4,173,415; and 4,188,121. Patents related to fluorescence techniques include U.S. Pat. Nos. 3,788,744; 4,225,229; and 4,243,318.

In 1965, Kamentsky et al were the first group to perform two parameter light measurements on cells by flow techniques. See Kamentsky et al; Spectrophotometer: New instrument for ultrarapid cell analysis, Science 150:630–631, 1965. In this work ultraviolet absorption by nucleic acids was measured while simultaneously analyzing light scatter. There are also many prior patents directed to multiple optical measurement, see U.S. Pat. Nos. 3,662,176; 3,850,525; 4,038,556; 3,824,402; 3,916,197.

The sensitivity of optical measurements is related to how much of the fluorescent light emitted by the particle can be collected, or how much of the incident light which is scattered or absorbed can be recollected. These parameters are related to the optical configuration of the instrument, including the numerical aperture (N.A.) of the lens system and whether the optical axis is parallel to or transverse to the stream of flow of the particles or cells.

Optical systems have been described for measuring fluorescence in a particle flow stream parallel to the optical axis (axial flow). Some such systems have advantageously used incident light illumination, where the same optics are used to introduce light to the particle flow and to collect the fluorescent light from the particles.

There have also been described optical transverse flow cytometers, where the flow of particles or cells is transverse to the optical axis. See, for example, U.S. Pat. Nos. 4,056,324; 4,225,229; 3,720,470; and SCIENCE, Vol. 204, 27 April 1979, page 403.

Axial Flow optical cytometers, although they have shown some very good results with fluorescence measurements, have several disadvantages. A light scatter parameter is not possible due to the difficulty in placing the detector behind the cells being measured. Secondly, an objective is necessary which has a significant depth of focus in order to focus through the cross stream trough onto the emerging cells or particles. This arrangement, because of the large depth of field, increases the vertical cell analysis volume significantly, thus limiting the rate at which cells can be analyzed. With the increased vertical cell analysis volume, two or more cells can be introduced into the analysis volume and detected as a single fluorescent pulse (coincidence problems). Finally, the axial flow design does not lend itself to cell sorting, because cells exiting the orifice are not caught in a laminar flow stream.

Transverse flow optical cytometers circumvent some of the problems associated with axial flow. First of all, light scatter is possible, since detectors can be placed around the incident light beam (i.e. from a laser) which intersects the transverse flow. With this arrangement, light scatter intensities can be measured orthogonally to the incident beam. However, these orthogonal systems measure fluorescence 90° to the incident light. The amount of fluorescence measured from a cell at this angle is minimized due to internal absorbance of the fluorescent light before it exits at right angles to the incident beam. This "darkfield" illumination is used because one is assured of the powerful incident laser light not interfering with the fluorescent signal measured at 90° to the incident light. Since these geometrics are used on water streams in air, the orthogonal flow optical cytometer must use dry objectives, which limit the numerical apertures to 0.7 or less.

ELECTRONIC PARTICLE VOLUME

The basic concept of electronic counting of particles suspended in a conducting fluid passing through a small aperture is disclosed in U.S. Pat. No. 2,656,508 to Coulter. In this, an electric field is applied across the aperture or orifice, so as to cause current flow therethrough.

This aperture current is disrupted when a particle passes through the aperture, producing a measurable pulse which is used to count the particle.

In 1958, Kubitschek in Electronic Counting and Sizing of Bacteria, *Nature* 182:234–235, 1958, attempted to relate the amplitude or area of the pulse to the size of the particle. A large number of publications followed which attempted to explain and characterize this relationship. In a 1969 article, Grover et al (Electrical Sizing of Particles in Suspension, *Biophys J.*, 9:13981414, 1969) described the "edge effects" caused by the compression of the electric field as it passes from a large volume through a small aperture. That article also described the hydrodynamic flow considerations and the relationship between the particle volume and the change in the current observed as the particle traversed the aperture.

Particle trajectory sensitivity has been a problem in electronic cell volume analysis. Attempted solutions to these problems have included hydrodynamic focusing of the particle stream by directing it along the axis of the aperture, making the aperture long with respect to its diameter, and electronically rejecting any pulse shapes which were not Gaussian. Hydrodynamic focusing has been a reasonably effective solution to trajectory sensitivity, although the requirement for precise centering of the particle injector with relationship to the aperture has resulted in transducer designs which are overly complex.

Other difficulties encountered in the design of electronic particle detection transducers include (1) bubbles from the sample, electrodes, or deaeration of the suspending fluid, (2) electrode products and their effect on biological cells by changes in cell pH and tonicity, (3) so-called "back cursor" pulses caused by particles which have already traversed the aperture circulating back within the region of the aperture outlet and (4) clogging of the aperture. The solution to the bubble and electrode problems have centered around isolating the electrodes in separate chambers. Electrode products are minimized by lowering the aperture current and providing bubble traps. Back-cursor pulses have been dealt with by electronic discrimination of the longer back cursor pulses, using a second orifice to prevent recirculation, or flushing the outlet chamber with particle fluid.

Aperture clogging has presented a significant problem to these devices. The apertures are usually 50 to 100 microns in diameter and clog easily. Back flushing, fluid and sample filtration, and even a miniature windshield wiper mechanism as described in U.S. Pat. No. 3,259,891 have all been tried, with for the most part unsatisfactory results.

The literature on electronic cell volume instruments includes various approaches using other than direct current through the aperture in order to try to obtain further information on the particles. These include a multi-frequency alternating current device, an alternating current device with electrodes inside the aperture, and combinations of alternating current and direct current to determine both changes in resistance and capacitance as a particle traverses the aperture.

COMBINED OPTICAL AND ELECTRONIC PARTICLE VOLUME INSTRUMENTS

It should be apparent that more useful information as to the characteristics of a particle or cell can be obtained by the use of both electronic and optical techniques, than by the use of either separately. In 1970, Leif, in A Proposal for an Automated Multiparameter Analyzer for Cells, *Automated Cell Identification and Sorting*, Academic Press, New York, 1970, pp 131–159, proposed an instrument which would perform multiple optical and electronic measurements. Subsequent literature describes several versions of such a device known as AMAC (Automated Multiparameter Analyzer for Cells). One version, known as AMAC I, is described by Leif and Thomas in Electronic Cell-Volume Analysis by Use of AMAC I Transducer, *Clin. Chem.* 19:853–870, 1973. That instrument was an axial flow, transmitted illumination device, suitable for light scatter and electronic measurements. While electronic measurements were achieved with this device, no optical measurements were ever performed.

Steinkamp et al, in A New Multiparameter Separator for Microscopic Particles and Biological Cells, *Rev. Sci. Instr.* 44:1301–1310, 1973, described a transducer for performing combined electronic and fluorescence measurements. However, the measurements were not made simultaneously. The electronic measurement was made first, then downstream 135 microseconds later the fluorescent measurement was made orthogonal to the cell flow.

Kachel U.S. Pat. No. 4,198,160 also describes a transducer for both electronic cell volume and fluorescent measurements. Kachel employed incident light illumination for fluorescence and used a hydrodynamic focusing injector to position the particles. It is possible with this configuration to measure both parameters closer to each other, but still not truly simultaneously.

The literature includes a description of an AMAC IV transducer, which is equivalent to the Steinkamp apparatus described above, with the inclusion of a water immersion objective to pick up the fluorescence orthogonal to the laser excitation of the particle stream. The water immersion objective has a larger numerical aperture than air objectives (1.0 vs. 0.7 or less) and hence increased the light gathering ability in the fluorescence measurement. Independent electronic and fluorescence measurements were made but no combined measurements were successful because of the time delay from the electronic to the optical measurement.

The prior art of combined electronic and optical measurements also includes U.S. Pat. Nos. 3,710,933, 3,675,768, and 3,770,349. U.S. Pat. No. 3,710,933 to Fulwyler et al describes a system in which the electronic and optical measurements are made sequentially, and not truly simultaneously. The U.S. Pat. Nos. 3,675,768 and 3,770,349 to Sanchez describe apparatus which is said to provide both electronic measurements and light absorption measurements.

All of the combined techniques discussed above have used circular apertures in a wall as the transducer. There is one report in the literature, however, of an experimental transducer utilizing a square aperture, although the method by which the square aperture was formed has not been published. This was the AMAC III transducer, described in R. A. Thomas et al, Combined Optical and Electronic Analysis of Cells With the AMAC Transducers, *Journal of Histochemistry and Cytochemistry*, Vol. 25, No. 7, pp. 827–835, 1977. That transducer used hydrodynamic focusing to direct the particle stream and orthogonal fluorescent detection to the laser excited stream. The light measurements were made in a miniature cuvette which was the electronic aperture, so that theoretically all measurements could be made simultaneously. Separate electronic and fluorescent measurements have been reported, but to date no report of simultaneous measurements have been made.

Several common problems have existed in prior art attempts at combined electronic and optical cytometry. Unless the measurements are truly made simultaneously, there is a coincidence problem involved in accurately related the two sequential measurements to the same particle. If it is attempted to truly make simultaneous electronic and optical measurements, conflicting design considerations are involved.

With the electronic measurement, the aperture resistance must be large compared to the inlet and outlet resistance. If this is not the case, the effective length (i.e. the distance during which the particle appreciably affects the current flow) becomes long and the coincidence rate becomes unacceptable. The particles must pass rapidly from a region of low current flux to a region of high current flux and back again to a region of low current flux. In addition, they must travel along a trajectory which avoids the "edge effects."

With the optical measurements the larger the numerical aperture (N.A.) the more sensitive is the measurement. That is, resolving power is directly proportional to N.A., image brightness is proportional to (N.A.)$^2$, and depth of focus is inversely proportional to N.A. However, a large N.A. implies a large acceptance angle, which dictates that the object being measured must be as close as possible to the collecting lens.

In any axial flow combined transducer configuration, the electronic and optical design configurations are at odds with each other, and concessions must be made which reduces the sensitivity of either or both measurements. For example, in order to maximize the outlet volume for electronic considerations, the objective must be moved away from the aperture, which results in either a decrease in N.A. or loss of simultaneity of measurement, or both. In the transverse flow geometry, downstream optics has been the only solution, which results in the loss of simultaneity of the measurements.

Of all of the prior art constructions, the AMAC III transducer came closest to solving the problems of combined electronic and optical measurements. In the AMAC III the square electronic aperture was also the optical aperture. By using a square geometry, the inlet and outlet chambers were large in volume with respect to the aperture volume, thus accommodating the electronic constraints. The square geometry, however, sacrificed N.A. by limiting the acceptance angle to 90° for the fluorescent measurement. The fluorescence was activated by an orthogonally disposed laser which sacrificed the light gained by incident light illumination, but produced good light scatter characteristics.

As can be seen from the foregoing abbreviated discussion of some of the prior art, the field of flow cytometry has and continues to be very active. An unquestioned need exists for a flow cytometer which can provide truly simultaneous electronic and optical measurements, without sacrificing any of the sensitivity possible with either technique. Additionally, the need exists for improved sensitivity in both electronic and optical measurement techniques.

SUMMARY OF THE INVENTION

Accordingly, it is an object of this invention to provide a method and apparatus for improved sensitivity flow cytometry.

It is another object of this invention to provide a method and apparatus for flow cytometry which simultaneously provides electronic and optical measurements.

It is another object of this invention to provide a flow cytometer transducer in which inlet and outlet geometries are such as to decrease electronic edge effects through the aperture while providing increased electronic sensitivity.

It is another object of this invention to provide an electronic and optical flow cytometer transducer formed of a plurality of solid polygons defining a polygonal aperture.

It is another object of this invention to provide a flow cytometer for simultaneous electronic and light scatter measurements.

It is another object of this invention to provide a flow cytometer for simultaneous electronic and optical measurements in which at least one of a plurality of elements defining the cytometer aperture is the first element in the optical system for making the optical measurements.

It is another specific object of one embodiment of this invention to provide a flow cytometer having a triangular transducer aperture.

It is another object of this invention to provide a flow cytometer and method in which sonication is used as a means for clearing a clogged aperture.

It is another object of this invention to provide a flow cytometer for simultaneous electronic and optical measurements in which incident light illumination and sensing is used for the optical measurements.

Briefly, in accordance with one embodiment of the invention, there is provided a flow cytometer having an aperture in which an inlet chamber and an outlet chamber are provided which have predetermined geometric relationships with respect to the aperture for decreasing electronic edge effects and increasing the sensitivity of electronic particle volume measurements. In accordance with one of the embodiments, the aperture is triangular and is formed by assembling a plurality of truncated pyramids with their truncated surfaces defining walls of the aperture. The inlet and outlet geometries formed by the truncated pyramids are configured to reduce edge effects from the flow of current through the aperture and to maintain a predetermined cross-sectional area relative to the cross-sectional area of the aperture. Electrodes are provided to establish current flow through the aperture, for electronic particle or cell volume measurements. At least one of the elements forming the aperture walls is either part of a lens system or a transparent cover plate for an oil immersion objective used in performing simultaneous optical measurements on particles or cells while they are in the aperture. These optical measurements can be fluorescence, light scatter, or both. Further, in accordance with one aspect of one embodiment of the invention, a piezoelectric transducer is provided to sonically clear any clogging of the aperture.

BRIEF DESCRIPTION OF THE DRAWINGS

FIG. 6 is a front elevation of one embodiment of a flow cytometer according to the invention.

FIG. 7 is a side elevation of the cytometer of FIG. 6.

FIG. 10 is a top plane view of truncated pyramids forming elements in the cytometer of FIG. 6.

FIG. 11 is a front elevation showing the truncated pyramids of FIG. 10 joined together.

FIG. 12 is a bottom view of the assembly of FIG. 11.

DETAILED DESCRIPTION

In its broadest aspect, the present invention contemplates providing an aperture or sensing zone for electronic or combined electronic/optical flow cytometers in which an inlet chamber and an outlet chamber are provided adjacent the aperture and which have predetermined geometric relationships to the aperture. The predetermined geometries of the inlet and outlet chambers in accordance with the invention decrease the electronic "edge effects" and also result in significantly increased sensitivity of electronic volume measurements of sample particles passing through the aperture.

Figure 1:
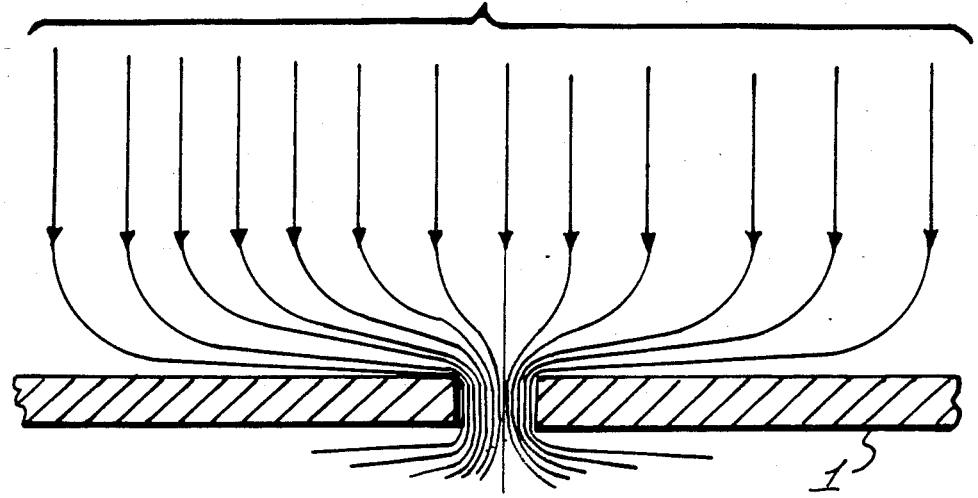
FIG. 1 is a cross-section of a flow cytometer aperture in accordance with the prior art, illustrating the current flux density edge effects.

The prior art of electronic particle volume counters has provided an aperture or sensing zone in the form of a small circular hole provided in a wall. FIG. 1 illustrates diagrammatically the pattern of the current flux density through such an aperture consisting of a circular hole through a wall 1. As can be seen, the current flux density has a tendency to bunch up at the edge of the circular hole. these "edge effects" are responsible for a large amount of false information when attempting to relate the magnitude of the change in current to the size or volume of the particle. For example, slight trajectory differences as particles traverse the measuring zone result in different amounts of current being blocked by identically sized particles.

In accordance with the present invention, an inlet and an outlet chamber are provided to the aperture which have chamber walls provided immediately adjacent the aperture that have a predetermined geometric relationship to the aperture.

Figure 2:
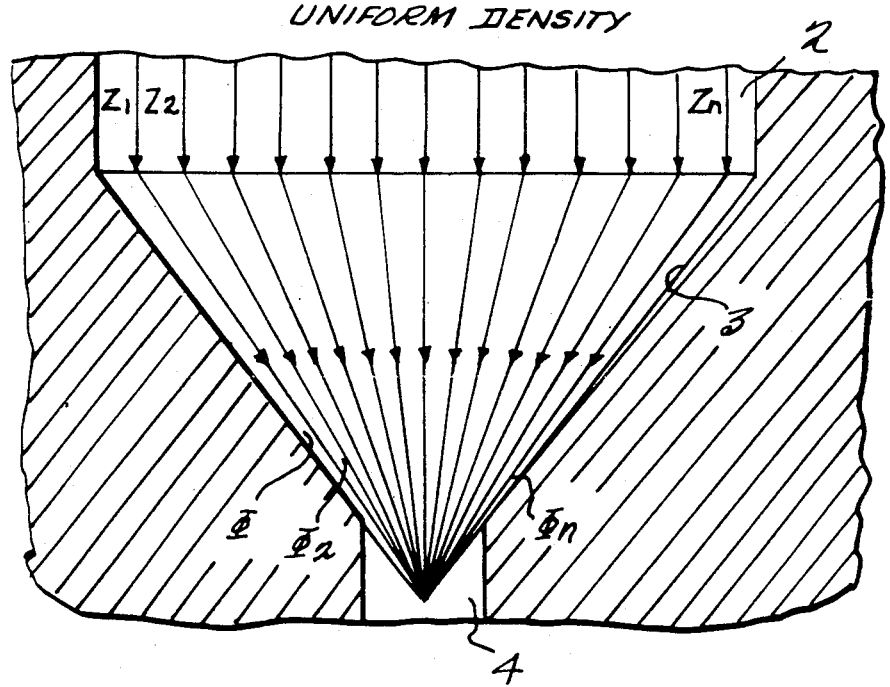
FIG. 2 is a schematic representation of a flow cytometer aperture having an inlet chamber with angled walls.
Figure 3:
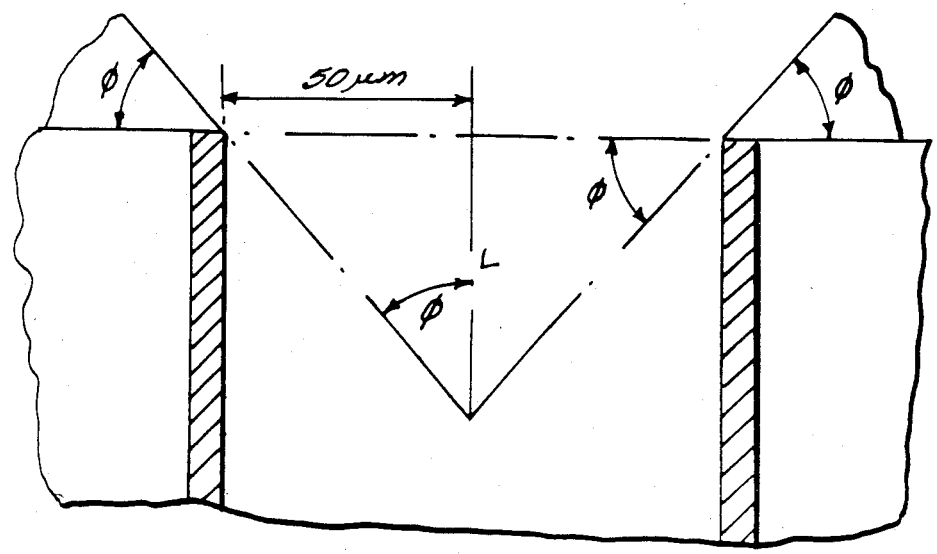
FIG. 3 is similar to FIG. 2 and illustrates various angular relationships concerning a flow cytometer aperture.

In accordance with a first aspect as shown in FIGS. 2 & 3 insofar as decreasing the edge effects, assume a chamber 2 where the current flux density is uniform. This chamber connects to an inlet chamber having walls 3 making an angle $\theta$ with respect to the plane of an aperture or measuring zone 4. Since current follows the line of least resistance, it is possible as a first order approximation to stipulate that the current flux passing through area $Z_1$ of chamber 2 will pass through the volume subtended by the angle $\Phi_1$ the current flux passing through $Z_2$ will pass through the volume subtended by $\Phi_2$, and correspondingly for $Z_n$ and $\Phi_n$. Hence, the number of degrees represented by $\Phi_n$ will be inversely proportional to the current flux passing through $Z_n$. For fixed values of $I_n$ (representing a percentage of the width of the measuring zone or aperture inlet), it is possible to calculate the number of degrees for each corresponding angle $\Phi_n$ for varying values of the angle $\theta$. For the prior art arrangement of the hole in the wall, $\theta$ equals zero. For $\theta$ equals to 90°, a measuring chamber with no inlet angle would be described.

Referring to FIG. 3, assume for the sake of discussion, that the aperture is 100 microns wide, and that an angle $\phi_{50}$ is defined as the angle formed from the center of the aperture to its edge (with the inlet chamber wall at an angle $\theta$). Additional angles $\phi_{40}$, $\phi_{30}$, $\phi_{20}$, $\phi_{10}$ are the angles formed between the center of the aperture and 40, 30, 20, 10 microns from the center, respectively. The distance L shown in FIG. 3 can be described in terms of $\theta$ by $$L = \tfrac{1}{2}\text{base}\tan\theta = 50\mu m \times \tan\theta \tag{1}$$

Therefore, the L can be determined by varying $\theta$. As the angle $\theta$ increases or decreases, the L values can be determined. Therefore, the flux line density can be described at the aperture entrance at arbitrary distances along the width of the aperture from the center by determining $\phi$ for a given $\theta$ (or L which is used in the calculation). These arbitrary distances can, for example, be multiples of I, which can be 10 μm.

The value for $\phi_n$ is then given by $$\phi_n = \tan^{-1}\frac{nI}{L} - \tan^{-1}\frac{(n-1)I}{L} \quad (2)$$

Table I given below shows the result of this approach. The entrance of the measuring zone or aperture has been broken into ten equal width segments, five to either side of the center of the aperture. The quantity $1/\phi_{10}$ represents a segment from the center moving toward the edge 10% of the width of the aperture; $1/\phi_{20}$ is from 10%–20% of the width; $1/\phi_{30}$ is from 20%–30%; $1/\phi_{40}$ is from 30–40% of the width; and $1/\phi_{50}$ is from 40–50%, i.e., the edge of the aperture.

TABLE I

Distance into the orifice (L) vs. the inverse of $\phi$ at various distances from the centerpoint at the beginning of the orifice At 10 μm from the center (I = 10)$\mu_m$ to the edge (I = 50$\mu_m$)

| $\phi$ | L | $1/\phi_{10}$ | $1/\phi_{20}$ | $1/\phi_{30}$ | $1/\phi_{40}$ | $1/\phi_{50}$ |
|---|---|---|---|---|---|---|
| 1° | 0.873 | 0.0118 | 0.402 | 1.205 | 2.381 | 4.000 |
| 2° | 1.746 | 0.0125 | 0.204 | 0.602 | 1.205 | 2.000 |
| 3° | 2.620 | 0.0133 | 0.139 | 0.405 | 0.806 | 1.333 |
| 4° | 3.496 | 0.0141 | 0.107 | 0.306 | 0.602 | 1.000 |
| 10° | 8.816 | 0.0206 | 0.057 | 0.135 | 0.253 | 0.412 |
| 20° | 18.199 | 0.0347 | 0.053 | 0.090 | 0.148 | 0.224 |
| 30° | 28.870 | 0.0523 | 0.064 | 0.088 | 0.124 | 0.172 |
| 40° | 41.955 | 0.0746 | 0.083 | 0.099 | 0.124 | 0.157 |
| 50° | 59.588 | 0.105 | 0.111 | 0.122 | 0.140 | 0.163 |
| 70° | 137.37 | 0.240 | 0.243 | 0.248 | 0.256 | 0.265 |
| 85° | 571.50 | 1.00 | 1.00 | 1.00 | 1.00 | 1.00 |
| 87° | 954.10 | 1.67 | 1.67 | 1.67 | 1.67 | 1.67 |
| 89° | 2864.5 | 5.00 | 5.00 | 5.00 | 5.00 | 5.00 |

As can be seen from Table I, for an inlet angle of 1° (essentially a hole in a wall) the variation in values $1/\phi_{10}$ to $1/\phi_{50}$ is quite large, with very large values near the edge, i.e., for $1/\phi_{50}$. As the inlet angle $\theta$ is increased, the dispersion (difference across the measuring inlet in current flux density) decreases. At a $\theta$ of 50°, the values are almost constant across $$\frac{1}{\phi_{10}} - \frac{1}{\phi_{50}}.$$

Figure 4:
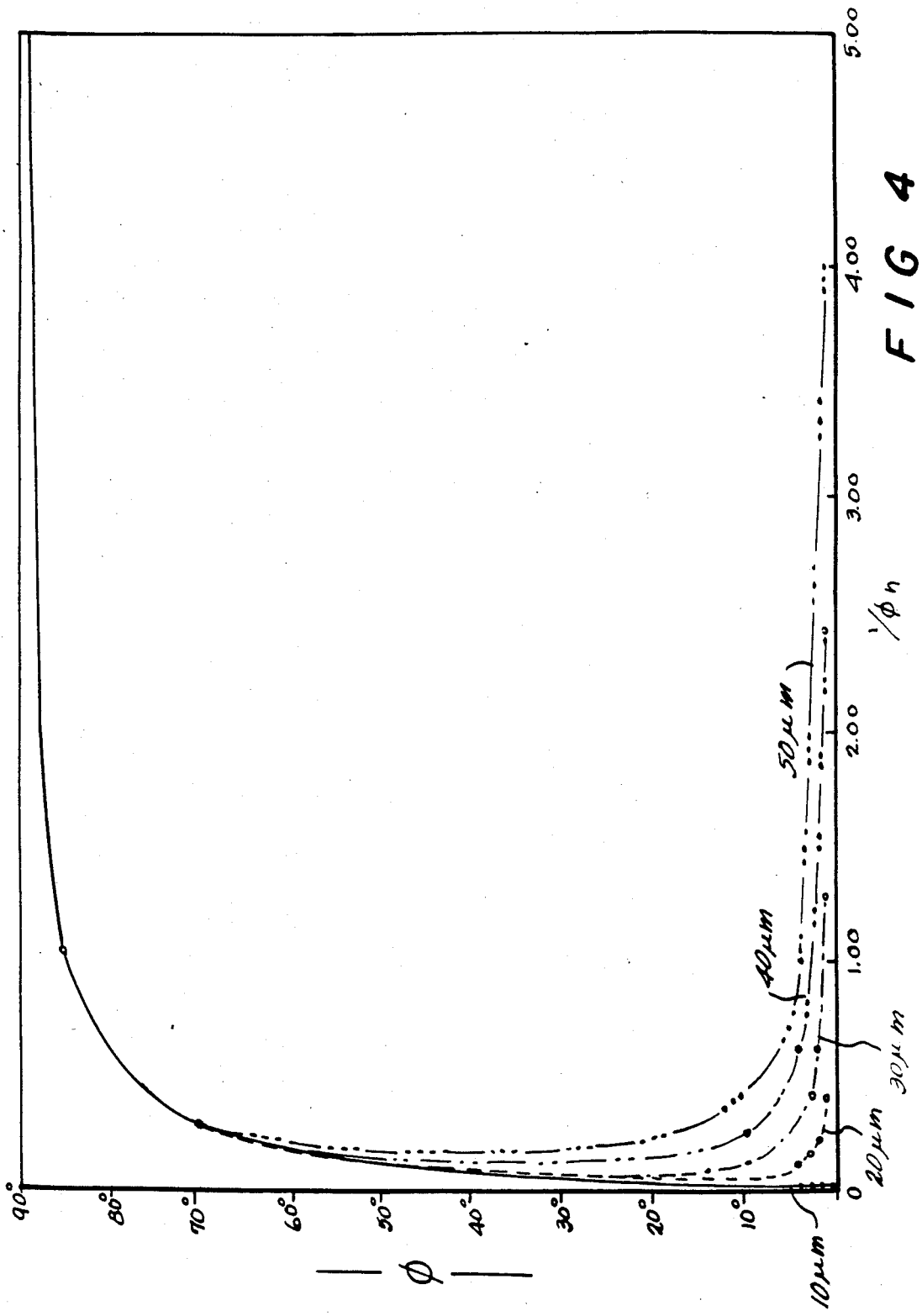
FIG. 4 is a graph illustrating edge effect current flux variations as the angle of the inlet chamber wall varies.

FIG. 4 is a plot of these values. As can be seen from FIG. 4, the curves converge at around 50° and remain converged to 90°. As can be seen from the curves of FIG. 4, significant reduction of the edge effects result from inlet chamber angles $\theta$ of 5° and greater. Thus, in accordance with this aspect of the invention, an inlet chamber is provided to the sensing chamber with the inlet chamber walls disposed at an angle of 5° or greater with respect to the plane of the aperture, for reducing edge effects. Like considerations apply to providing an exit chamber whose walls are disposed at an angle of 5° or greater with respect to the plane of the aperture.

In addition to decreasing edge effects in electronic particle volume cytometers, it is desirable to have as sensitive an instrument as possible. The current flux density in the aperture is inversely proportional to the cross-sectional area. Hence, when the particle is confined to a small geometrical cross-section, the current flux interrupted by the particle will be maximized. Therefore, as the particle is travelling toward the measuring zone (i.e., the place where the current flux density is maximized), it is desirable for it to pass rapidly from a region of low current flux density to a region of high current flux density, i.e., to rapidly pass from a zone where it makes no appreciable change in the current to a zone where the change in current is a maximum.

Figure 5:
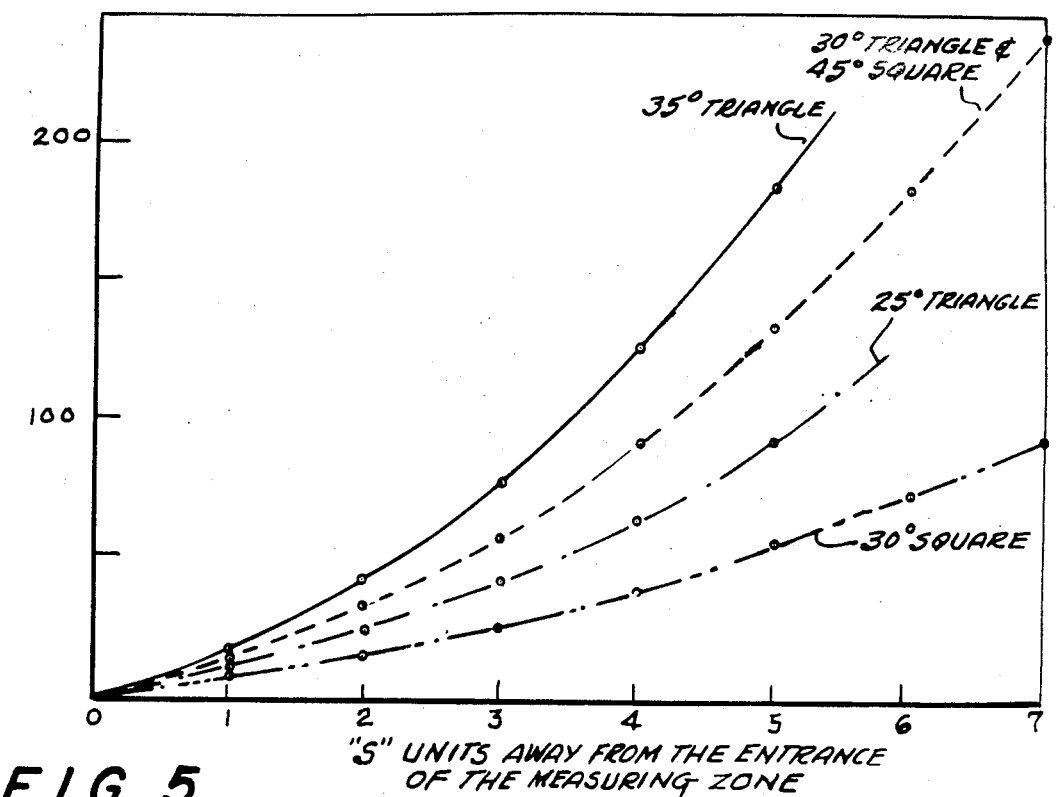
FIG. 5 is a graph of the ratio of the inlet chamber cross-section to the aperture cross-section for various distances into the inlet chamber, for various configurations of inlet chambers.

In accordance with the principles of this invention, inlet and outlet chambers are provided adjacent either side of the sensing aperture, with the cross-sectional area of the inlet and outlet chambers having a predetermined relationship to the cross-sectional area of the aperture. First, a size parameter, which will be called an "S" unit, is defined as the maximum linear dimension or width of the aperture along any plane passing through the axis of the aperture. In accordance with this aspect of the invention, the aperture can have any cross-sectional geometric configuration, i.e., circular, square, triangular, etc. It has been experimentally determined that at a linear distance of two "S" units measured from either side of the aperture into the inlet and outlet chambers, that the cross-sectional area of the inlet and outlet chambers at these points should be greater than ten times the cross-sectional area of the aperature. (See FIG. 5) If the cross-sectional areas of the inlet and outlet chambers at these points is greater than ten times the cross-sectional area of the aperture itself (and preferably on the order of twenty-thirty times as much in cross-sectional area), it has been found that sharp, well-defined, electronic particle volume pulses from the electronic cytometer result.

In accordance with another aspect of this invention, an improved method has been found for constructing electronic and/or optical sensing apertures for flow cytometers by cooperative relationship of a plurality of solid polygons. The terms "solid polygons" is meant to refer to a multi-sided three-dimensional polygonal shape. A plurality of these solid polygons are provided having surfaces which function to define the aperture or sensing zone, and also having surfaces defining the geometry of the inlet chamber and the outlet chamber so that they have predetermined geometric relationships with respect to the aperture or sensing zone, in accordance with the broader aspects of the invention. It is within the scope of the invention to provide such an assembly in which the aperture is triangular, square, 5-sided, etc. A triangular aperture is, however, the preferred embodiment for the many advantages it provides. For making optical measurements, at least one of the elements defining the walls of the aperture is part of an optical system. In accordance with the invention, the at least one element which is part of an optical system can be a transparent cover plate against which, i.e. an oil immersion objective is situated, or can itself be a lens forming the first optical element in an optical system. If desired, it is within the scope of the invention to provide more than one of the elements defining the walls of the aperture, even all of them, as a part or parts of an optical system for either introducing exciting light into the sensing zone in the aperture or collecting light therefrom.

Figure 8:
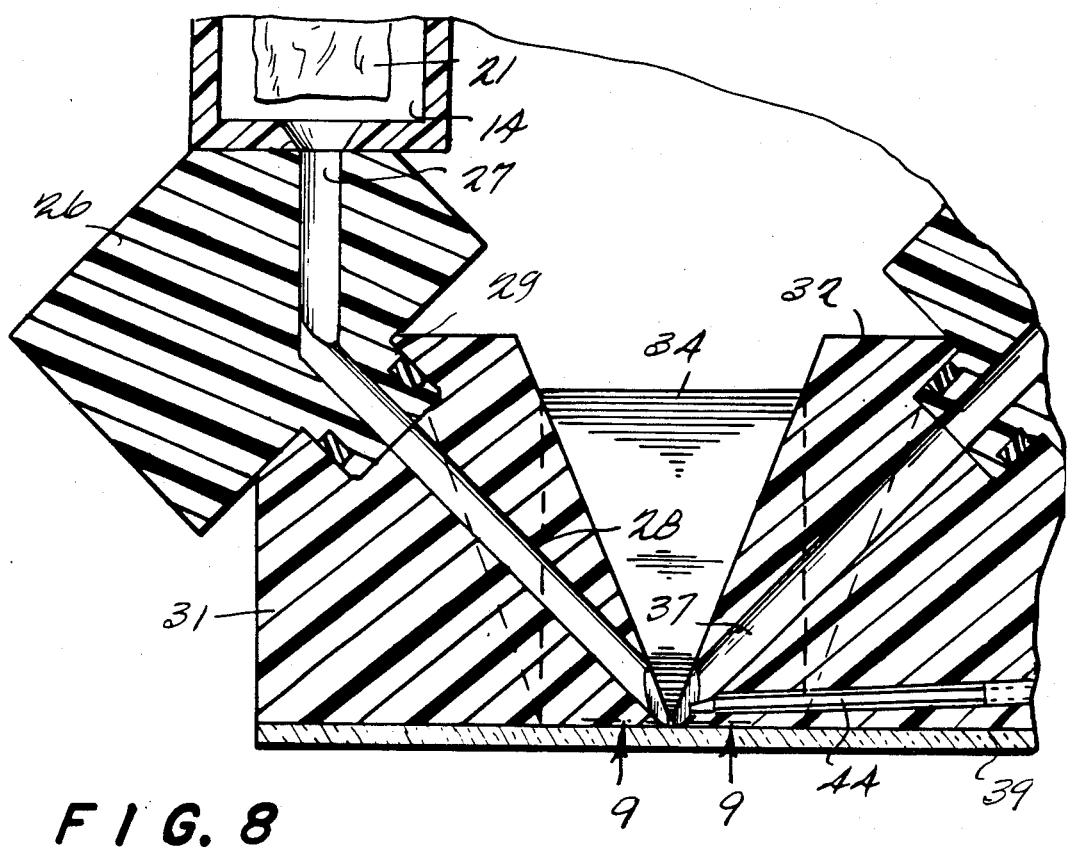
FIG. 8 is a cross-section of a portion of the cytometer of FIG. 6.
Figure 9:
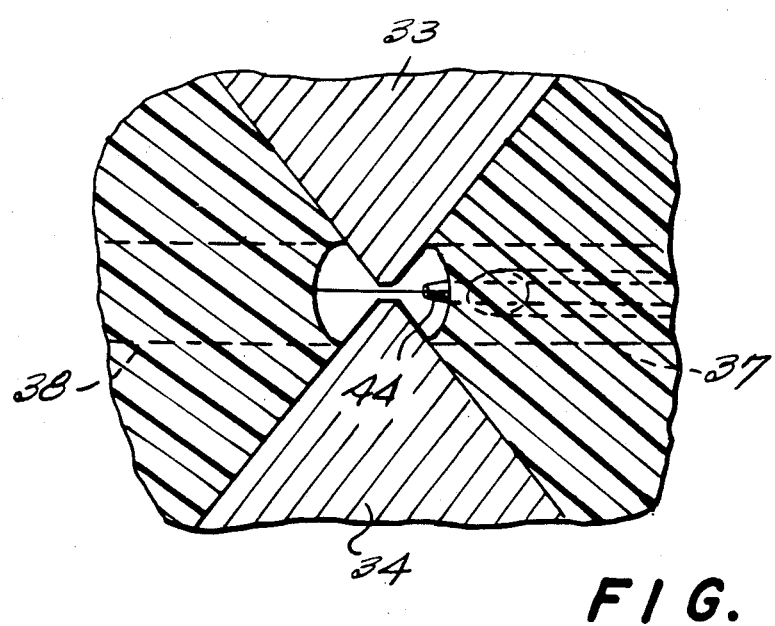
FIG. 9 is a cross-section along the line 9—9 of FIG. 8.
Figure 13:
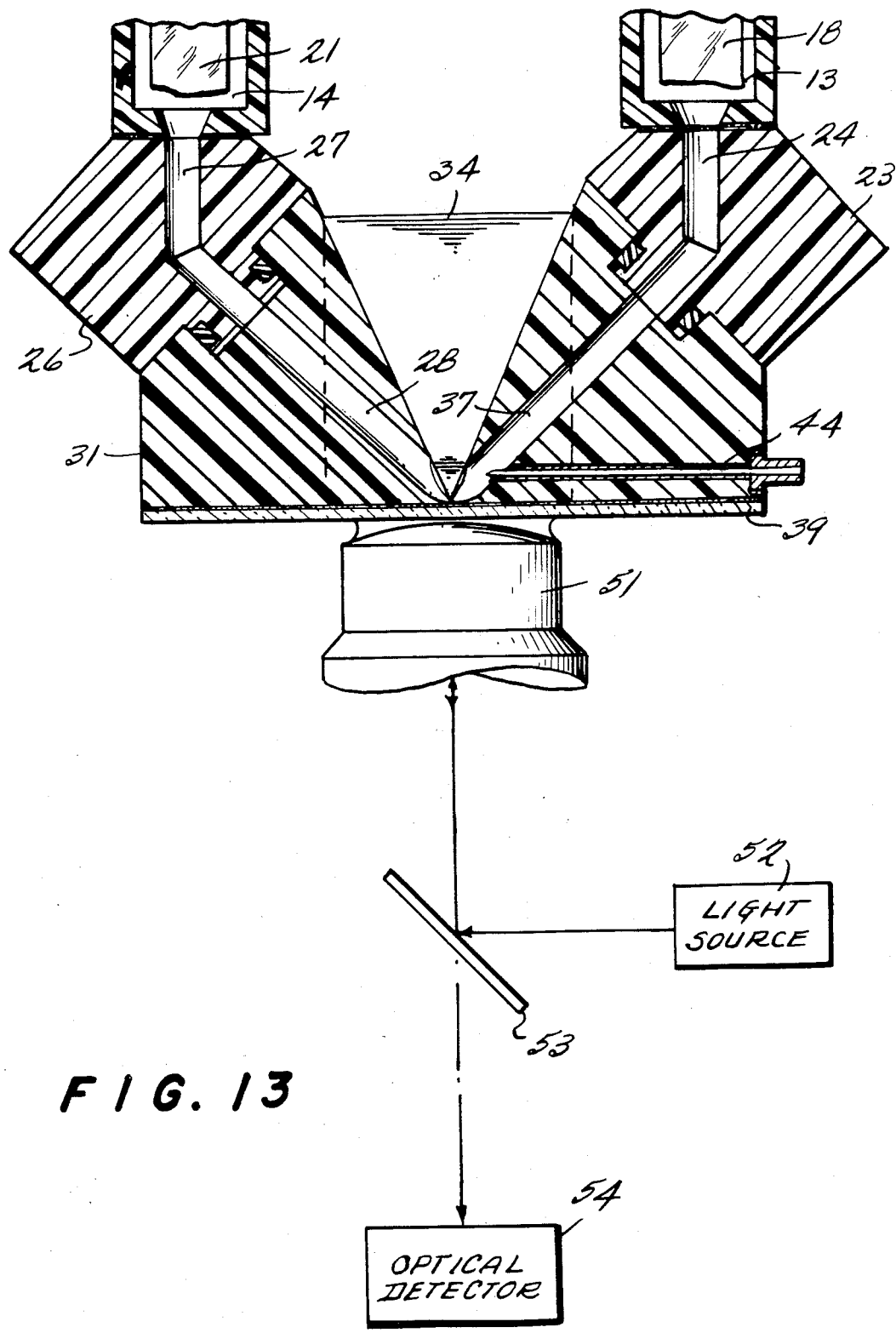
FIG. 13 is partly a cross-section of a portion of the cytometer of FIG. 6 and illustrates diagrammatically an optical sensing arrangement as part of the cytometer.

FIG. 6 shows a front elevation of a portion of an actual apparatus constructed in accordance with principles of the present invention. FIG. 7 is a side elevation thereof, and FIGS. 8, 9 and 13 are various sectional views thereof. In the drawings, a mounting plate 11 mounts via a clamp member 12 two electrolyte reservoirs 13 and 14. The electrolyte reservoir 13 is in communication with a suitable source of electrolyte through conduit 16. The electrolyte reservoir 14 is coupled through its conduit 17 to a repository for used electrolyte, which may include a vacuum source or the like for establishing a negative pressure. Altlernatively, a pressure can be coupled to the inlet reservoir to establish the required pressure differential between the inlet and outlet reservoirs. Disposed within the reservoir 13 (which is the electrolyte supply side of the device) is an electrode 18. The electrode 18 can be foil electrode or the like and is electrically connected to a lead 19. In a similar fashion, the reservoir 14 has mounted therein an electrode 21 which is electrically connected to a lead 22.

Attached to the bottom of reservoir 13 is a housing 23. The housing 23 has a passageway generally indicated by reference numeral 24 formed therein, which is in communication with the interior of reservoir 13. Similarly, a housing 26 is provided mounted to the bottom of reservoir 14 and having a passageway generally indicated by reference 27 numeral therein, which is in communication with the interior of reservoir 14. The housings 23 and 26 have O-ring assemblies 28 and 29, respectively.

The O-ring assemblies 28 and 29 plug into and mount ceramic blocks 31 and 32. A glass solid polygon 33 is adhesively secured to surfaces 31a and 32a of the ceramic blocks 31 and 32. As used herein, the term "solid polygon" is meant to refer to a multisided three dimensional geometric shape. In a similar fashion, another solid polygon 34 formed of glass is adhesively secured to opposite surfaces of the ceramic blocks 31 and 32 (see sectional view in FIG. 7.)

In a manner more fully discussed hereafter, the glass solid polygons 33 and 34 cooperate to define an aperture at a sensing zone generally indicated by reference numeral 36 in FIG. 6. Further, in a manner more fully discussed hereafter, the solid glass polygons 33 and 34 are configured so as to provide inlet and outlet chambers to the aperture which have a predefined geometric relationship to the dimensions of the aperture.

The ceramic block 32 is provided with an inlet passageway 37 which couples the passageway 24 to the inlet chamber defined by the glass solid polygons 33 and 34. In a similar fashion an outlet passageway 38 extends through the ceramic block 31 to couple an outlet chamber defined by the glass polygons 33 and 34 to the passageway 27.

In the specific arrangement shown in and described, two flat surfaces of the solid glass polygons 33 and 34 define two walls of a triangular aperture at the sensing zone 36. If desired, an identical third solid glass polygon could be provided to form the third wall of the triangular aperture and the third wall of inlet and outlet chambers. In accordance with the specific embodiment illustrated in the drawings, however, a differently configured solid glass polygon in the form of a glass cover plate 39 is provided adhesively secured to the solid glass polygons 33 and 34 and the ceramic blocks 31 and 32 and functioning to define the third wall of the triangular aperture at the sensing zone 36 and the third wall of the inlet and outlet chambers. In this specific embodiment, a coupling 41 is illustrated which is adapted to couple a microscope objective, such as an oil immersion objective, for optical viewing of the sensing zone 36 through the glass cover plate 39.

As shown in the drawings, the ceramic block 32 has an additional sample inlet passageway 42 which mounts through a suitable O-ring assembly 43 a sample injector 44. The sample injector 44 extends into the passageway 37 adjacent the beginning of the inlet chamber defined by the solid glass polygons 33 and 34. The sample injector 44 is adapted to be coupled to a sample source of particles or biological cells or the like, in a manner well known to those skilled in the flow cytometry art. It should be noted as shown in the drawings, that the sample injector extends at an angle with respect to the flow path of electrolyte through passageway 37 and the inlet chamber defined by solid glass polygons 33 and 34. Suitable provision is made via, for example, the O-ring assembly 43, for longitudinally adjusting the sample injector 44 so as to position it at various points in the stream of electrolyte flowing through passageway 37 and the inlet chamber defined by the solid glass polygons 33 and 34.

In accordance with a particular aspect of one embodiment of the invention, a sonicator in the form of a piezoelectric crystal 46 is provided attached to the mounting plate 11 and having suitable leads 47 for connection to a source of electrical power. Also as part of the sonication apparatus, a spring assembly 48 can be provided.

The manner in which the solid glass polygons 33 and 34 cooperate to define the polygon shaped aperture and the inlet and outlet chambers can best be understood by referring to FIGS. 10, 11 and 12. FIG. 10 shows the solid glass polygons 33 and 34 which, in accordance with this specific embodiment, are truncated pyramids. As illustrated, the solid glass polygon 33 has four sides 33a, 33b, 33c, and 33d. In a similar fashion, the solid glass polygon 34 (which ca be identical to 33) has four sides 34a, 34b, 34c and 34d. Each of the solid glass polygons 33 and 34 have truncated portions generally indicated by 33e and 34e. As shown in FIG. 11, the two solid glass polygons 33 and 34 can be joined together by adhesively securing the surfaces 33d and 34d to one another, with the solid glass polygons in aligned relationship. When this is done, the truncated portions 33e and 34e define (as shown in this particular example) two walls or sides of a triangular shaped sensing aperture. To the arrangement of FIG. 11, and referring to FIG. 6, the glass cover plate 39 is then attached to the bottom of the assembly shown in FIG. 11 to define the third wall o side of the triangular shaped sensing aperture. It should be clear from FIGS. 10, 11 and 12, that the truncated portions 33e and 34e define both the cross sectional area of the sensing aperture and its depth, so that they fix the volume of the sensing aperture.

As apparent from the drawings, adjacent surfaces 33c and 34a define the volume and cross-sectional area of either an inlet chamber or an outlet chamber, and the corresponding adjacent surfaces 33a and 34c define the other of the inlet or outlet chambers.

Referring back to FIGS. 6-9, the manner in which the illustrated device generally functions is as follows. A flow of electrolyte is established through the sensing zone 36 (a triangular aperture in this specific embodiment) from the electrolyte reservoir 13 and back up into electrolyte reservoir 14. This flow of electrolyte is established by means such as a vacuum source connected to the conduit 17 of reservoir 14. A source of electric potential A.C. and/or D.C. is connected between leads 19 and 22 so that a current flow is established through the electrolyte between electrodes 18 and 21 via the various passageways and the sensing zone or aperture 36. Samples, such as particles or biological cells are injected into the flow of electrolyte through the sample injector 44. As the samples are injected into the flow of electrolyte going through the aperture or sensing zone 36, upon passage through the aperture they affect the electrical resistance between electrodes 18 and 21 in a manner well known to those versed in the art of flow cytometry generating pulses indicative of particle volume measurements.

In accordance with one aspect of the invention, as more fully discussed hereafter in connection with FIG. 13, simultaneous optical measurements can be made on a particle or biological cell as it is traversing through the aperture or sensing zone 36. That is, the glass cover plate 39 itself forms one of the walls of the aperture and is part of an integral optical system focused o the particle or cell while it is in the aperture. In this manner, truly simultaneous electronic and optical measurements can be made on the same exact particle, and no correlation problems arise.

The angles and dimensions of the various surfaces on the solid glass polygons 33 and 34 influence both the fluidic flow characteristics and the electrical field characteristics through the sensing zone or aperture 36. As known in the art, it is important to have laminar flow of the electrolyte containing the samples through the sensing zone or aperture in order to minimize turbulence which would disrupt the position of the particles in the sensing zone. It has been found that the triangulated laminar flow sheath provided by the triangular aperture and triangular inlet and outlet zones formed in accordance with one embodiment of the invention, provides exceptional positional stability to an injected stream of particles injected via sample injector 44.

The angle of the walls of the inlet and outlet chambers influence both the fluidic flow characteristics and the electrical field characteristics of the device. The inlet and outlet chamber shapes can be calculated to produce a continuous fluidic boundary layer from inlet, through the sensing zone, and through the outlet chamber, in order to minimize turbulence. In addition, this shape produces a smooth transition from a region of low current flux (i.e. the inlet chamber) to a region of high current flux (i.e. the sensing zone or aperture) and back to a region of low current flux (i.e. the outlet chamber). This smooth transition decreases the "edge effects" which an abrupt transition from large volume to small volume (i.e. the prior art provision of a hole in a wall) induce. By limiting the edge effects, the particle will encounter a region of uniform current flux during its transit through the aperture or sensing zone. This leads to improved sensitivity of the electronic measurements.

In accordance with the broader aspects of the invention, the walls of the inlet and outlet chambers are configured such that they make an angle of 5° or greater with respect to the plane of the aperture in order to decrease the edge effects. Further in accordance with the broader aspects of the invention the walls of the inlet and outlet chambers are configured such that at a distance of two "S" units away from the sides of the sensing aperture the cross-sectional area of the inlet and outlet chambers is at least ten times greater than the cross-sectional area of the aperture. These geometric considerations dictate the limit conditions for the geometries of solid polygons used to define the aperture and the inlet and outlet chambers in accordance with that aspect of the invention.

In accordance with the embodiments of the invention wherein solid polygons are used to define the aperture and the inlet and outlet chambers, as discussed previously truncated pyramids have been found to be advantageous geometries for the solid polygons, although it is not intended to be limited thereto. Using truncated pyramids, either a triangular aperture and inlet and outlet chambers can be formed by assembling three identical truncated pyramids, or a square aperture and inlet and outlet chambers can be configured by assembling four truncated pyramids. FIG. 4 is a plot of the ratio between the cross-sectional area of the inlet chamber to the cross-sectional area of the aperture versus "S" units away from the entrance of the aperture or sensing zone for triangular and square orifices assembled by joining a plurality of truncated pyramids. The angular references on the curves in FIG. 4 refer to the angles made by the flat walls of the inlet and outlet chambers with respect to the axis of the aperture. Using curves like those of FIG. 4, the angles for the truncated pyramids used to assemble the transducer can be calculated in accordance with the desired relationship between the inlet and outlet chamber cross-sections and that of the aperture, in accordance with the principles of this invention. As can be seen for the case of the triangular aperture with a 30° inlet angle, at two "S" units away from the measuring zone, a particle influences the current by about three percent of the maximum value. This is derived by the ratio of 31/1 of inlet cross-sectional area to measuring zone crosssectional area. Therefore, a particle in the measuring zone will experience a three percent coincidence error by a following particle which is two "S" units away from the measuring zone.

In the specific embodiment of the invention shown in FIG. 6, the walls of the two truncated pyramids defining two walls of the inlet and outlet chambers were oriented at 50° with respect to the plane of the aperture, leading to negligible edge effects in the electronic measurements. Further, the ratio between the cross-sectional areas of the inlet and outlet chambers at two "S" units from the aperture sides was approximately 40 to 1. This was found to result in sharp, well defined electronic particle volume pulses.

It should be apparent from the drawings, that in accordance with specific embodiments of the invention the flow of electrolyte containing samples from the inlet chamber through the aperture or sensing zone and out the outlet chamber is an arch-shaped flow, with the aperture or sensing zone at the vertex or "knee" of the arch. This is important from the standpoint of optical sensing. As clear from the drawings, optical sensing is through the glass plate 39 forming one of the walls of the sensing zone. Since the particle path is arched, the particles in the sensing zone remain in focus as they traverse across the optical path through the aperture or sensing zone. Particles which either have not yet reached the sensing zone or which are leaving the sensing zone are not in focus, and hence do not interact with the optical measurement of particles in the sensing zone.

In accordance with one particular feature of one embodiment of the invention, the sample injector 44 is not coaxially centrally located, as has been the case in the prior art. Rather, the sample injector is brought in at an angle to the triangulated flow sheath of the electrolyte. As the particle injector is moved from edge to edge of the triangulated flow sheath, the position of the particles in the sheath and hence in the sensing zone or aperture is changed. In this manner, precise positioning of the sample stream in the electrolyte in order to further minimize electronic field edge effects experienced by the particle stream can be accomplished.

The provision of a triangular-shaped sensing zone or aperture, besides the advantages it offers by way of imparting exceptional stability to the triangulated flow sheath, has other advantages. In electronic detection of particle characteristics, the volume of the sensing zone or aperture (i.e. the cross sectional area times the length) is one of the determining factors in the sensitivity of the measurement. For a small particle you need a small cross section for greatest sensitivity. The smaller the cross section, however, the greater is the tendency to clog. Hence it is advantageous to have a small cross-section yet as large as possible a dimension across the cross section, in order to decrease clogging. For the case of an equilateral triangle, the longest dimension is 1.35 times as great as a circle with the same cross sectional area. In accordance with a specific embodiment of the invention, the triangular orifice or aperture was such that it was 100 microns on a side and 100 microns long.

The geometry of a triangular aperture also offers significant advantages with regard to optical measurements on particles in the aperture. The sensitivity of any optical measurements is related to how the quantity of total light, which is emitted from the particle, can be collected, or how much of the incident light, which is scattered or absorbed, can be recollected. Using a triangular aperture sensing zone, for the case of an equilateral triangle, 120° per side of light gathering can be achieved in the axis of the plane of the triangular cross section. In the axis perpendicular to that, 180° is available, depending on the geometry of the inlet hole.

One method of establishing a practical optical boundary is by considering the state of the art in available microscope objectives. To date, high quality objectives have a Numerical Aperture (N.A.) of 1.25 to 1.4. The N.A. is given by the formula:

$$N.A. = n_0 \sin \theta$$

where $n_0$ is the index of refraction of the object space and $\theta$ is the half angle of acceptance of light. Since these lens are maximized to work in an objective space of $n_0 = 1.515$, then a range of $\theta$ may be determined for these lens, i.e., N.A. $= 1.25 = 1.515 \sin \theta$.

$$\sin \theta_L = \frac{1.25}{1.515} = .825$$

$$\sin \theta_U = \frac{1.4}{1.515} = .92$$

$$N.A. = 1.25, \theta_L = 55°$$

$$N.A. = 1.4, \theta_U = 67°$$

so a practical optical geometrical limit for the best commercially available microscope optics is a half angle of light acceptance between 55° and 67°. This fits right in the range of acceptance angle provided by one side of a triangular aperture.

In accordance with one specific embodiment of the invention shown in FIG. 13, in which the optics are indicated in diagrammatic form, oil immersion objective 51 is provided adjacent the glass cover plate 39, and focused on the sensing zone or aperture 36. A suitable light source 52 is provided for introducing exciting light into the sensing zone via means such as beam splitter 53. Assuming that fluorescent measurements are to be made with respect to samples in the sensing zone 36, the light source 52 can either be a mercury bulb or a laser, emitting light, for example, in the ultraviolet spectrum. In any event, the exciting light is introduced through the oil immersion objective 51 into the sensing zone or aperture 36. Assuming that the samples flowing through the aperture or sensing zone 36 have been properly prepared, i.e. stained or the like in the case of biological cells, they will emit characteristic fluorescent light. This light is collected by the oil immersion objective 51 and passed through the beam splitter 53 to an optical detector 54, such as a photo multiplier tube or the like. Since in the specific embodiment being discussed the aperture is triangular, light is collected by the oil immersion objective 51 over an acceptance angle of 120°, providing a N.A. of 1.3. As an alternative to providing the glass cover slip 39 as part of the optical system, the element defining that wall of the aperture or sensing zone can be a lens itself.

In the descriptions of the solid polygons 33 and 34 and cover plate 39, they have been referred to as "glass." No particular limitation is intended by the use of such term, the point being that the elements defining the walls of the sensing aperture have optical qualities such that they can form part of a system for making optical measurements with respect to particles in the sensing aperture. In a particular embodiment, the solid polygons 33 and 34 were made from optical flats of BK7 glass, with precision lapping at desired angles to form the desired truncated pyramids. Whatever the material chosen for the solid polygons 33 and 34, care should be taken to use a material for the blocks 31 and 32 (FIG. 1) that has an equivalent thermal coefficient of expansion.

In the description of FIG. 7, reference was made to a piezoelectric crystal 40. It has been found that providing such a sonication apparatus is a very effective means of clearing any clogs that might arise in the sensing aperture 36. Temporarily applying electrical power to the piezoelectric crystal set up sonic vibrations through the electrolyte in the cytometer, and has been found to be very effective in clearing clogs that occur at the sensing aperture 36. As an alternative to providing a piezoelectric crystal affixed to the cytometer mounting plate as shown in FIG. 7, a piezoelectric crystal or other sonication producing element can be coupled to the sample injector 44. This would serve to set up localized sonication in the electrolyte near the sensing aperture 36.

Figure 20:
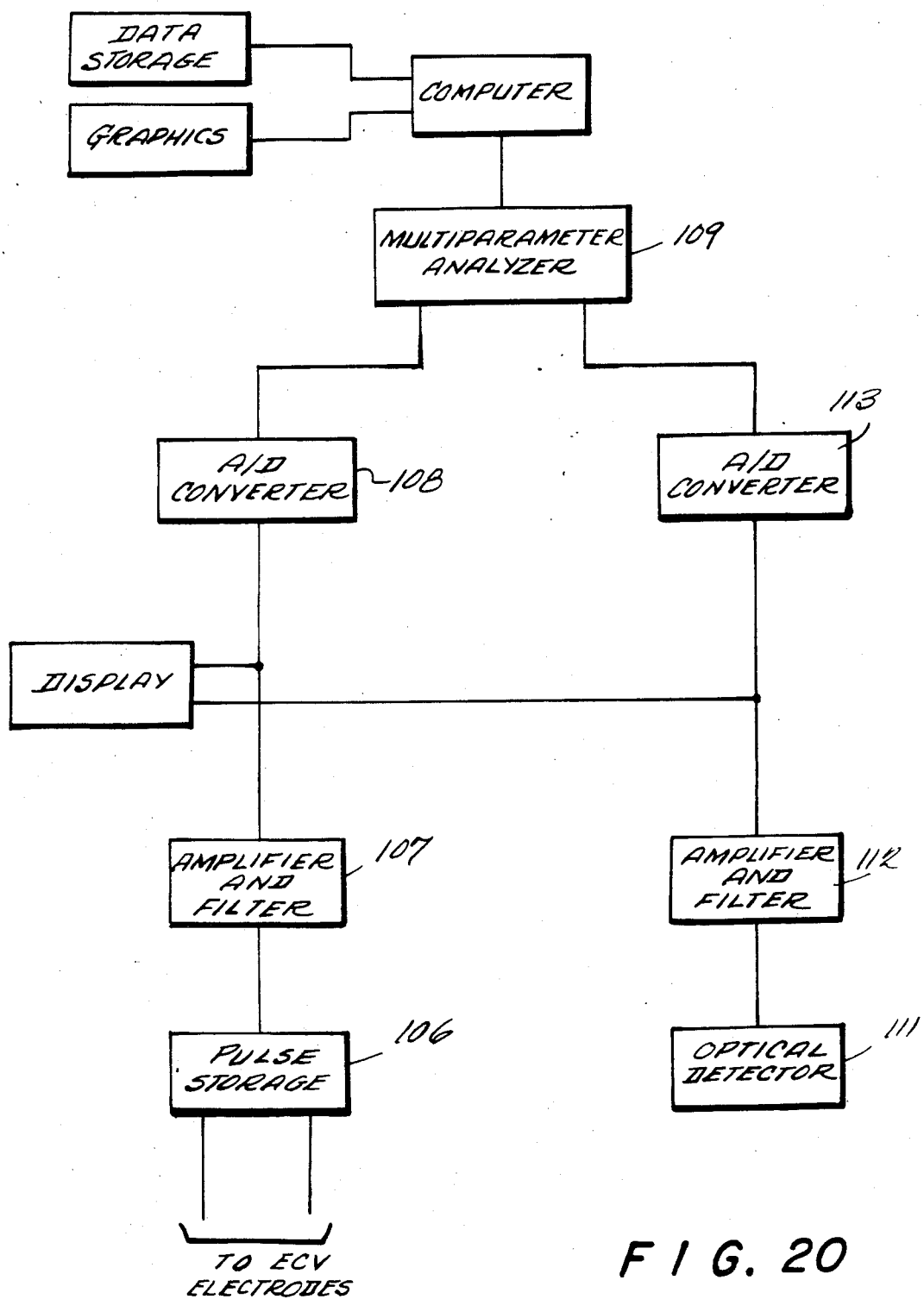
FIG. 20 is a block diagram of suitable electronics for use with the cytometer of the present invention.

Suitable electronic circuits for processing, recording and displaying data from the electronic and optical measurements are described in the literature and known to those skilled in the flow cytometry art. FIG. 20 illustrates in block diagram form one exemplary electronic arrangement suitable for this purpose. The electronic channel can include pulse storage and shaping circuitry 106, followed by amplifier/filter circuitry 107, and an analog to digital converter 108 which couple the electronic measurement signal into a multiparameter analyzer 109. The optical channel includes a suitable optical detector 111, coupled through amplifier/filter 112 and analog to digital converter 113 to the multiparameter analyzer 109. If desired, a real time display circuit 114 can be provided to provide a display of the relatively unprocessed signals from the electronic and optical channels.

FIG. 20 illustrates only one optical channel feeding into the multiparameter analyzer 109. Of course, if more than one optical detector is employed as in various of the embodiments of the invention, a corresponding plurality of optical channels can be provided.

As is conventional, the multiparameter analyzer 109 inputs to a suitable computer 116 which can perform various data manipulation and correlation. Connected to the computer can be data storage means 117 and a graphics means 118 for providing graphs and the like.

Figure 14:
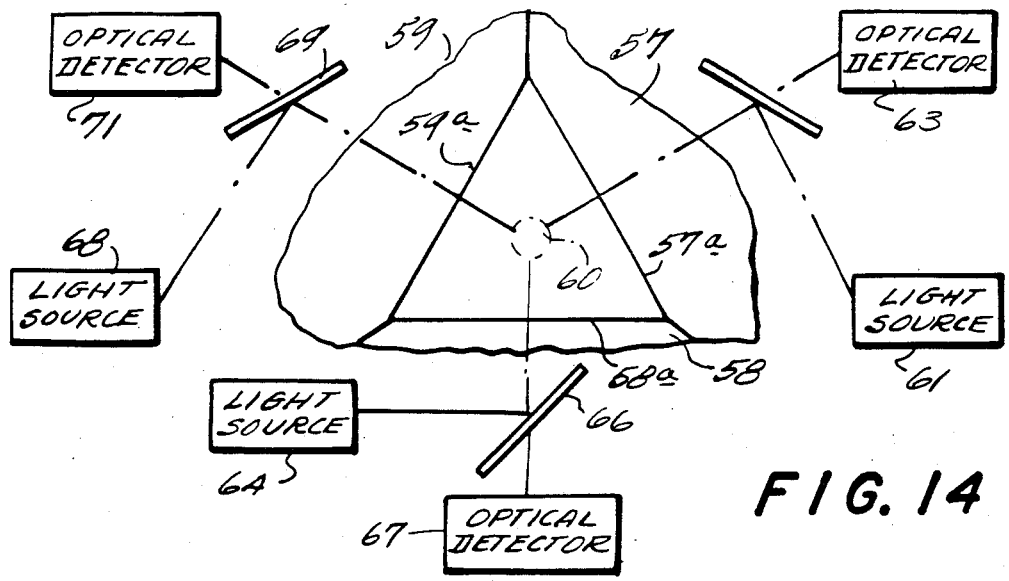
FIG. 14 is a diagrammatic representation of a flow cytometer optical sensing arrangement in accordance with one embodiment of the invention.

FIG. 14 is a diagrammatic representation of one of the many possible alternate embodiments of this invention in which more than one side of the triangular aperture or sensing zone can be used for making optical measurements. In FIG. 9 the triangular aperture or sensing zone 56 is shown as formed by flat surfaces of three solid polygons 57, 58 and 59. The solid polygons 57, 58 and 59 can be made of glass and have flat surfaces 57a, 58a, and 59a defining the walls of the triangular aperture or sensing zone 56. The solid polygons themselves can be ground so that they function as lenses for the respective sides 57a, 58a, and 59a of the aperture. Such additional lens elements as necessary can be provided in the optics for the three sides of the aperture 56, but are not shown in FIG. 14 for simplicity. Referring to the side of the aperture defined by surface 57a, means can be provided for introducing exciting light into the aperture to excite a particle (indicated by the dashed line 60) by means of a light source 61 and a beam splitter 62. Means such as an optical detector 63 are provided for detecting the light emitted by particle 60 through the wall 57a of the aperture 56.

In a similar fashion, means can be provided in the form of a light source 64 and a beam splitter 66 for introducing exciting light into the aperture through the wall 58a thereof. Likewise, an optical detector 67 can be provided for detecting the light emitted by the particle 60 through the wall 58a of the aperture. In the same fashion, a light source 68 and beam splitter 69 can be provided for introducing exciting light through the wall 59a of the aperture. Means such as an optical detector 71 can be provided for detecting the light emitted by the particle through the wall 59a.

The light sources 61, 64, and 68 can all be identical, i.e. ultra violet sources, for fluorescent measurements or the like on the particle 60, or they can be different. Further, if desired, only one light source can be provided, with detectors being provided on two or all three sides of the aperture 56. The point is that by collecting light on all three sides of the aperture 56, an effective N.A. of three times the N.A. for one side, i.e., 3.9, can be achieved, vastly improving the sensitivity of optical measurements.

Various different schemes for using only one light source and one optical detector, while at the same time increasing the effective N.A. are possible. Thus, in FIG. 14, only the one light source 64 and one optical detector 67 could be provided for introducing exciting light through the aperture surface 58a and collecting light from the particle 60 through the surface 58a. To increase the effective N.A., the surfaces 57a and 59a can be mirror surfaces or the other surfaces of the polygons 57 and 59 can be mirrored, so as to reflect all light emitted by the particle 60 back through the surface 58a of aperture 56 for detection by the optical detector 67. Alternatively or additionally, the mirrored surfaces can function to reflect portions of the exciting light onto the particle 60.

Figure 15:
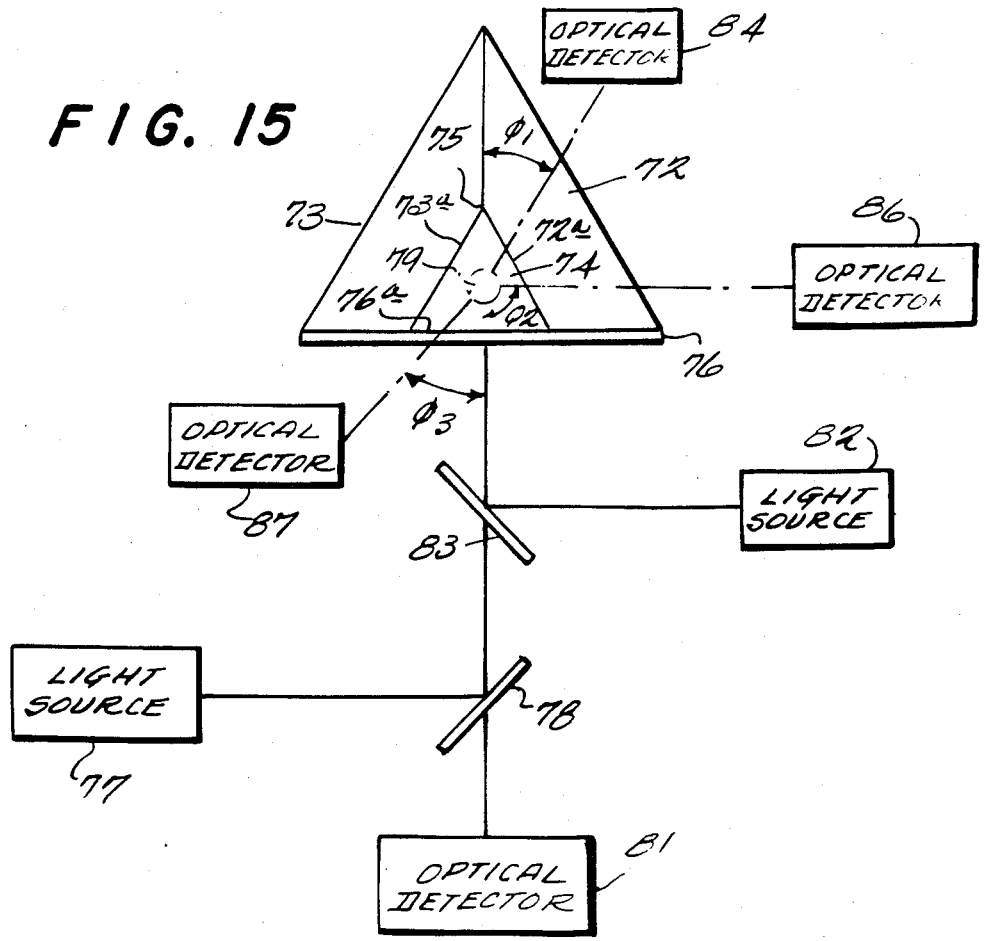
FIG. 15 is similar to FIG. 14 and illustrates another embodiment of an optical sensing arrangement.
Figure 16:
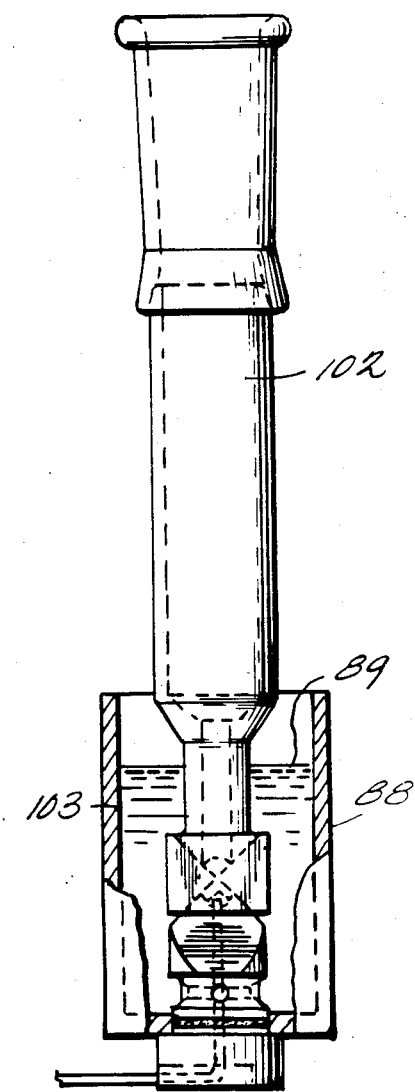
FIG. 16 is a front elevation partly in section of a transducer for an electronic flow cytometer.
Figure 17:
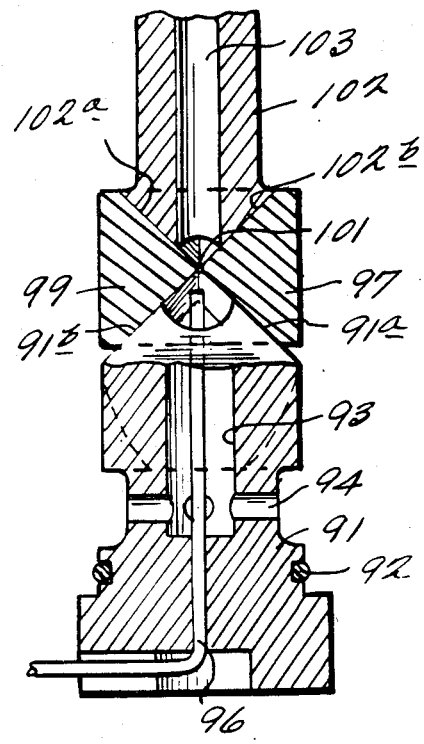
FIG. 17 is a section of a portion of the transducer of FIG. 16.
Figure 18:
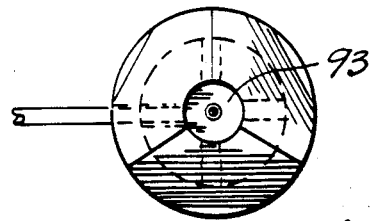
FIG. 18 is a view along the axis of the inlet chamber of the transducer of FIG. 16.
Figure 19:
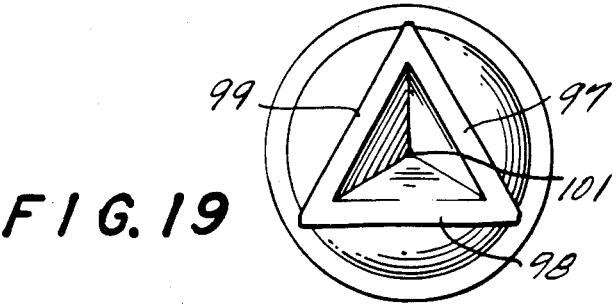
FIG. 19 is a view showing the triangular inlet chamber and aperture of the transducer of FIG. 16.

Turning to FIG. 15, there is shown still another possible embodiment of the invention in which light scatter measurement techniques are combined with fluorescent measurement techniques. In FIG. 15, solid polygons 72 and 73 are provided having flat surfaces 72a and 73a defining two walls of a triangular aperture or sensing zone 74. In the specific embodiment shown in FIG. 15 a glass cover plate 76 is shown as constituting the third wall 76a of the aperture 74, although it should be understood that instead of the glass cover plate 76 another solid polygon could be provided. With regard to the fluorescent measurement, a light source 77 and beam splitter 78 combine to focus light from the light source 77 through suitable optics (not shown) through the wall 76a onto particles (such as indicated by dashed line 79) in the aperture or sensing zone 74. Assuming that the particle has been suitably prepared by staining or the like, fluorescent light emitted by the particle is focused through the suitable optics (not shown) on an optical detector 81. Thus far, the optical system functions like that shown and described in reference to FIG. 13. Additionally, however, provision can be made for simultaneously making light scatter measurements with respect to the particle or sample 79. In this, provision can be made for a light source 82 and beam splitter 83 to couple suitable light, such as red laser light, through the wall 76a of the aperture 74. Multiple detectors, such as illustrated by optical detectors 84, 86 and 87 can be positioned at various angles $\theta 1$, $\theta 2$, and $\theta 3$ around the periphery of the elements defining the transducer for respectively detecting, for example, forward light scatter, 90° light scatter and back scatter. Advantageously, for the forward light scatter measurement, the apex of the triangular aperture (reference numeral 75) functions as a field stop.

By incorporating an arrangement such as schematically shown in FIG. 15 into the apparatus of FIG. 6, it can be seen that electronic particle volume, fluorescence, and light scatter measurements can all be made simultaneously on the same particle or cell sample in the sensing zone or aperture.

The important advantages of a triangular orifice or sensing zone in accordance with the principles of this invention are applicable to not only combined electronic and optical cytometers as discussed above, but are also applicable to purely electronic flow cytometers. FIGS. 16–19 pertain to an embodiment of the invention suitable for use in existing electronic flow cytometers. In this embodiment a supply reservoir housing 88 has a supply of electrolyte 89 disposed therein. An inlet housing 91 is provided mounted to the bottom of the supply reservoir housing 88 and suitably fluid-tight sealed with respect thereto by means such as O-ring 92. The inlet housing 91 has a centrally located inlet reservoir 93 which communicates via passageways 94 with the electrolyte 89. A sample injector 96 is provided centrally located in the inlet reservoir 93. Three truncated pyramids 97, 98 and 99 are adhesively secured to each other such that their truncated portions define an aperture or sensing zone 101 which is triangular in shape. As is the case in the other embodiments of the invention, the angular walls of the truncated pyramids 97, 98, and 99 define an appropriately configured inlet zone and outlet zone with respect to the aperture 101. An upper part of the inlet housing 91 is provided with angular surfaces 91a, 91b, etc., which match the angles on the mating surfaces of the truncated pyramids 97, 98 and 99, with these truncated pyramids being adhesively secured to the surfaces 91a, 91b, etc. An outlet housing 102 is provided having a centrally located outlet reservoir 103. The bottom portion of the outlet housing 102 is provided with surfaces 102a, 102b, etc., which match the mating services on the truncated pyramids 97, 98 and 99, with the mating surfaces being adhesively secured. As can be seen in the drawings, the sample injector 96 is positioned such that samples are injected into the center of the inlet chamber defined by walls of the truncated pyramids 97, 98, and 99, so as to traverse through the center of the aperture or sensing zone 101.

In operation, in a manner known to those skilled in the flow cytometry art, suitable means such as a vacuum source are coupled to the outlet housing 102 for establishing a flow of the electrolyte 89 from the supply reservoir 88 through the inlet reservoir 93, the aperture or sensing zone 101, and out the outlet reservoir 103. Suitable means such as electrodes and a source of electric potential are provided for establishing a current flow through this electrolyte. Samples injected from the sample injector 96 enter the flow sheath of the electrolyte and pass through the central portion of the aperture or sensing zone 101. This changes the electrical current through the aperture 101 and causes pulses which are detected by suitable electronics well known to those skilled in the flow cytometry art.

The advantages of the triangular aperture are very much applicable to the electronic measurement in the device shown in FIGS. 16-19. The triangulated flow sheath of electrolyte is exceptionally stable in its laminar flow characteristics through the aperture 101. The sample stream therefore passes through the aperture 101 in a very laminar manner, without any turbulence. Configuring the angles of the truncated pyramids defining the orifice 101 in a manner consistent with the principles of this invention produces a smooth transition from a region of low current flux in the inlet chamber to a region of high current flux in the aperture, and back to a region of low current flux in the outlet chamber. This smooth transition decreases the edge effects. Furthermore, in a manner discussed previously, configuring the inlet and outlet chambers to have a predetermined cross-sectional area relative to the cross-sectional area of the aperture in accordance with the principles of this invention, reduces the "effective" electronic length of the sensing zone and yields sharp, well-defined pulses. This produces much sharper electronic pulses occasioned by the passage of a particle or a sample through the aperture or sensing zone.

Referring now to FIGS. 21 through 33, there is presented a number of examples of various tissues prepared for DNA and/or electronic cell volume analysis utilizing one embodiment of a flow cytometer transducer in accordance with this invention. Specifically, this data was obtained using the flow cytometer illustrated in FIG. 6.

Figure 21:
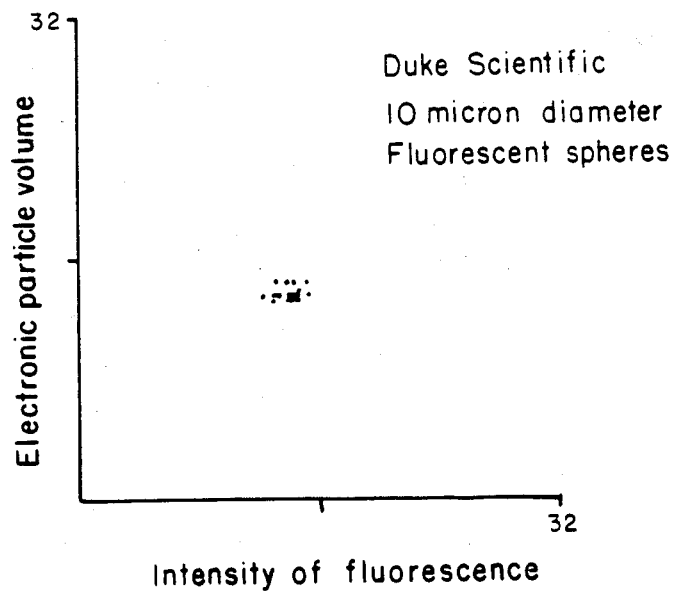
FIG. 21 is a combined electronic particle-fluorescence histogram of Duke Scientific 10 micron diameter fluorescent spheres.
Figure 22:
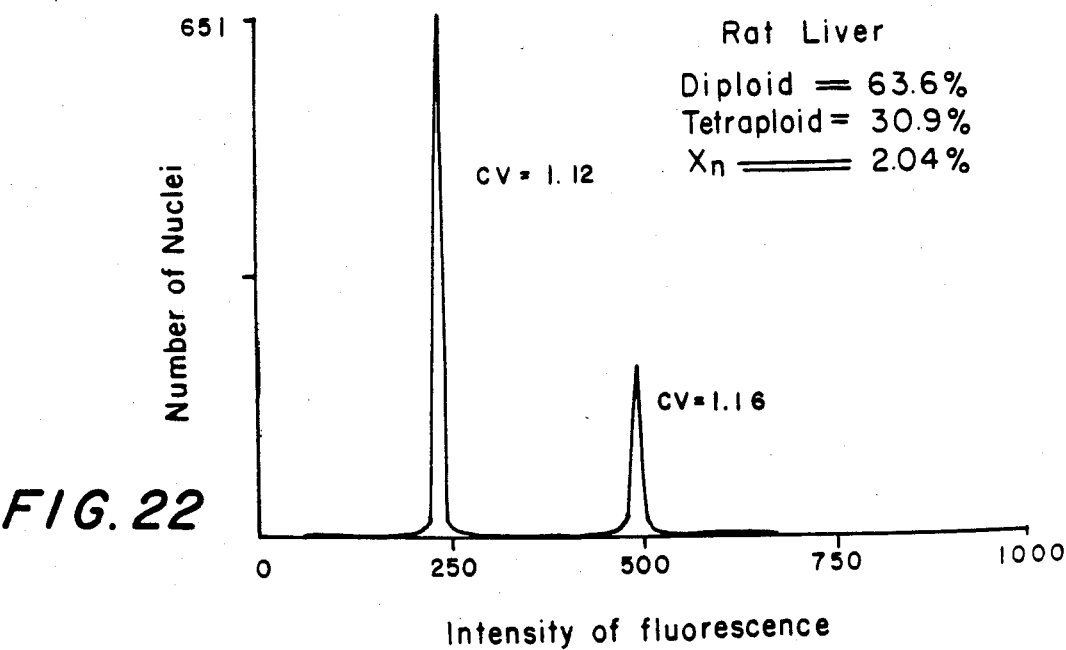
FIG. 22 is a flow cytometric DNA histogram of nuclei from Wistar rat liver.
Figure 23:
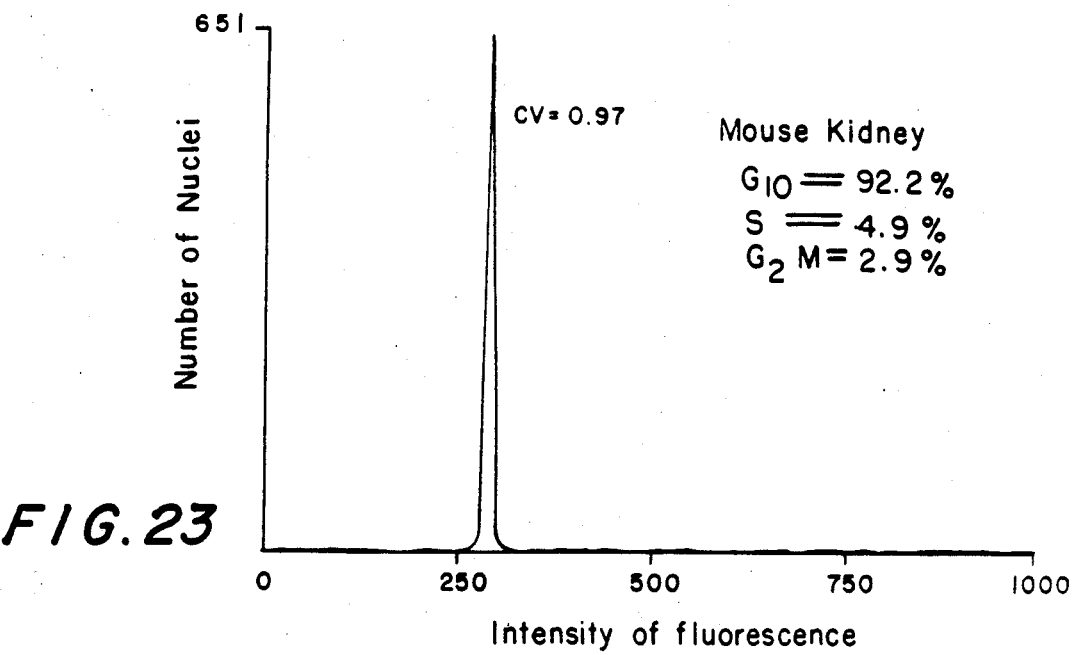
FIG. 23 is a flow cytometric DNA histogram of nuclei from normal CF1 mouse kidney.
Figure 24:
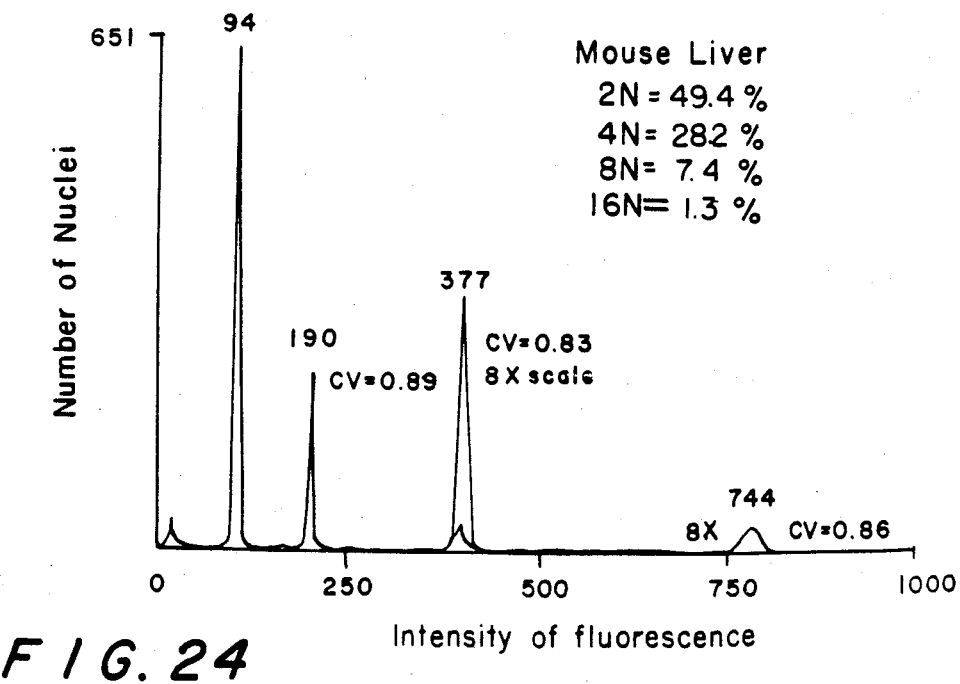
FIG. 24 is a flow cytometric DNA histogram of nuclei from normal CF1 mouse liver.
Figure 25:
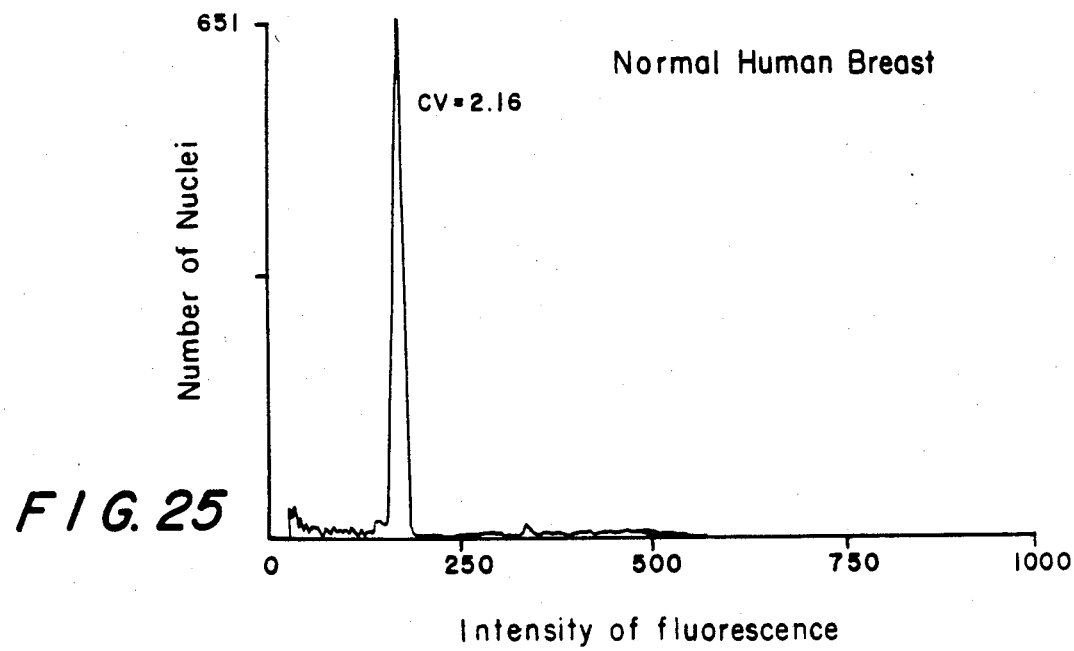
FIG. 25 is a flow cytometric DNA histogram of nuclei from normal human breast tissue.
Figure 26:
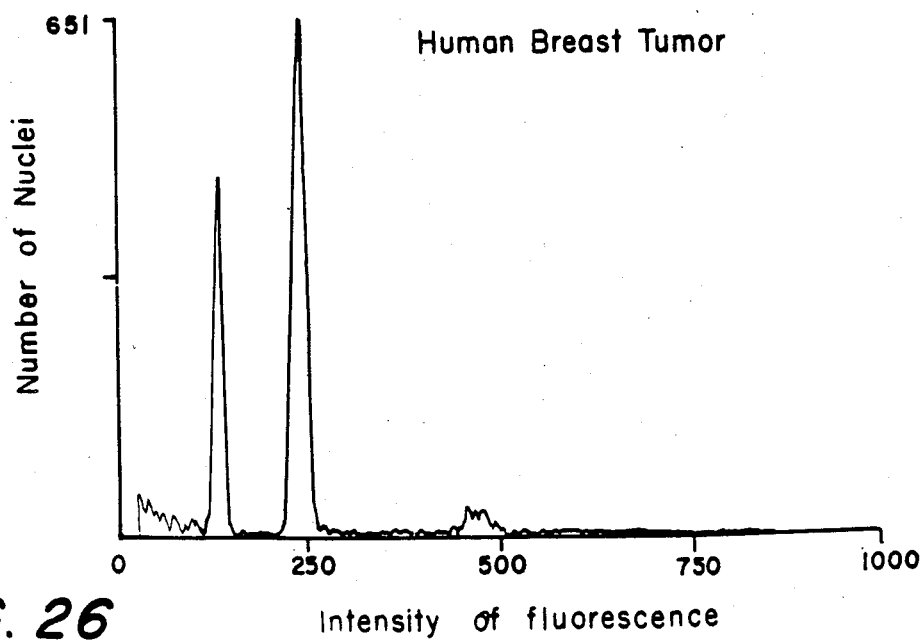
FIG. 26 is a flow cytometric DNA histogram of nuclei from a patient with breast cancer.

FIG. 21 is a combined electronic particle volume and fluorescence (530 nm) histogram of Duke Scientific 10 micron diameter fluorescent spheres. FIGS. 22-26 show DNA histograms (i.e. fluorescence measurements) of mouse, rat and human origin. Thus, FIG. 22 is a flow cytometric DNA histogram of nuclei from Wistar rat liver; FIGS. 23 and 24 are similar DNA histograms of nuclei from normal CF1 mouse kidney and liver, respectively; FIG. 25 is a flow cytometric DNA histogram of nuclei from normal human breast tissue; and FIG. 26 is a flow cytometric DNA histogram of nuclei from a patient with breast cancer.

All of the tissue samples used for the data of FIGS. 22-26 were prepared utilizing a nuclear isolation medium which contained DAPI, a DNA specific dye. The nuclear isolation medium utilized is disclosed in a patent application filed Apr. 24, 1981 in the name of Jerry T. Thornthwaite, and entitled "Nuclear Isolation Medium and Procedure for Separating Cell Nuclei". As can be seen from FIGS. 22-26, the coefficient of variation ranged between 1-2% for the DNA histograms, illustrating the efficacy of the optical aspect of the transducer of this invention.

Figure 27:
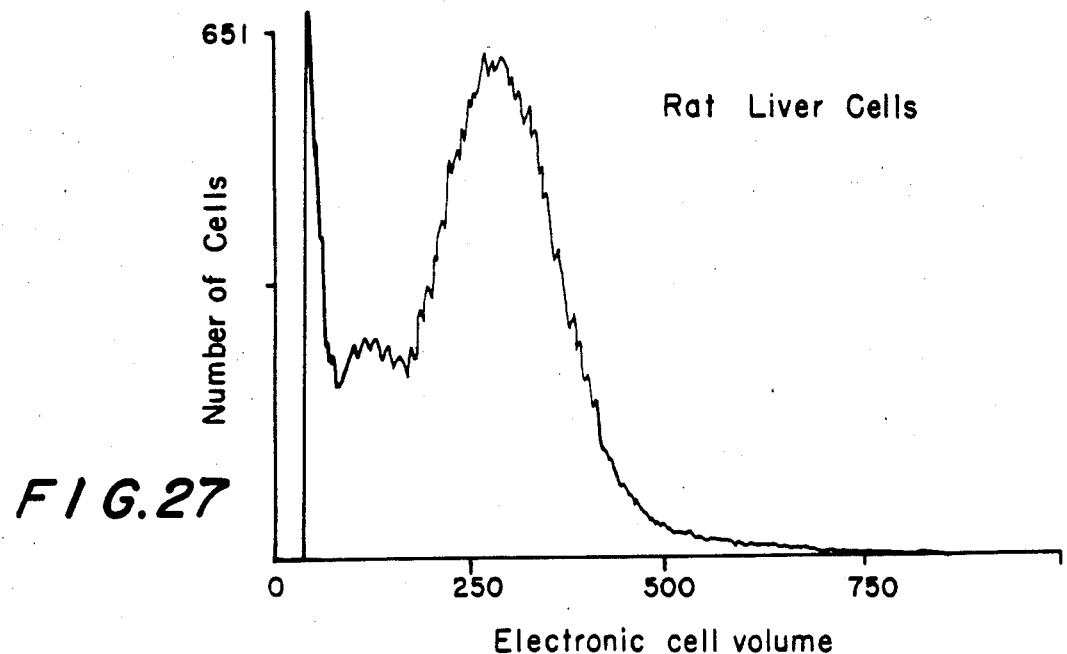
FIG. 27 is an electronic cell volume plot of Wistar rat liver dissociated with enzymes.

FIG. 27 is an electronic cell volume histogram of Wistar rat liver cells, which were enzymatically dissociated with collagenase and trypsin, and measured with the transducer of this invention.

Figure 28:
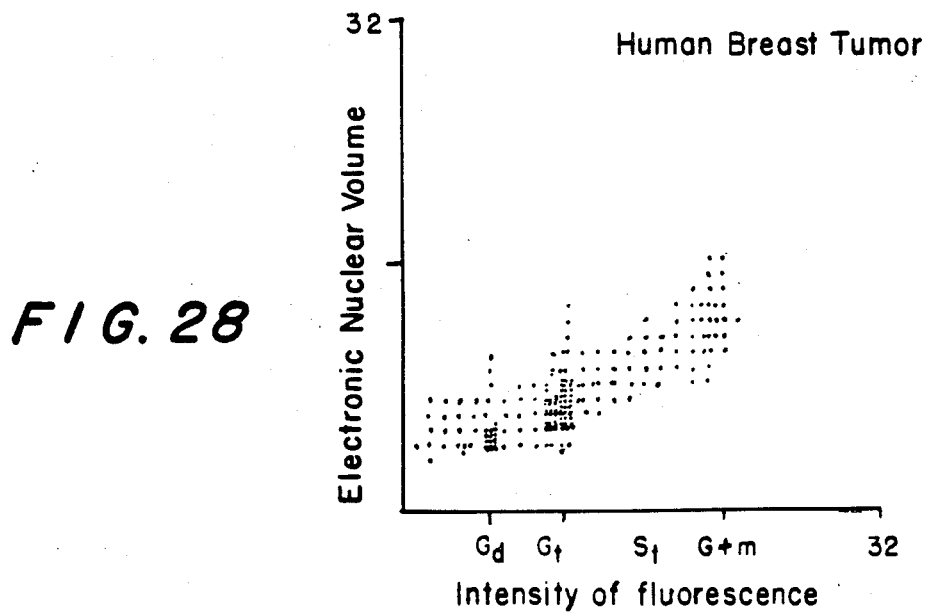
FIG. 28 is a combined plot of electronic nuclear volume and DNA fluorescence of nuclei from a patient with breast cancer.
Figure 29:
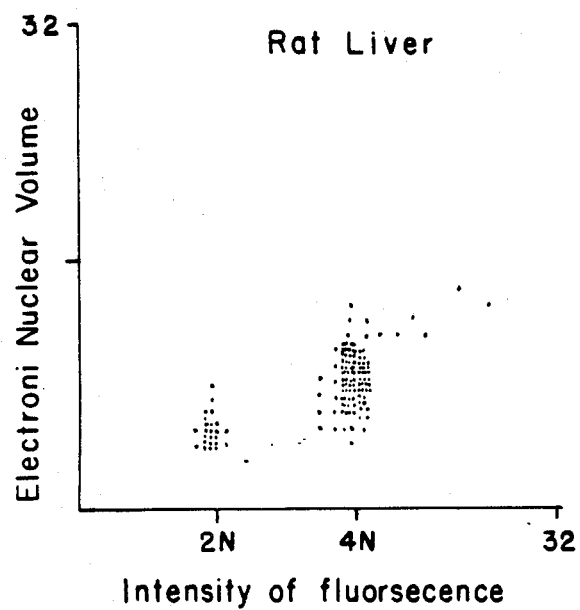
FIG. 29 is a combined plot of electronic nuclear volume and DNA fluorescence of nuclei from Wistar rat liver.
Figure 30:
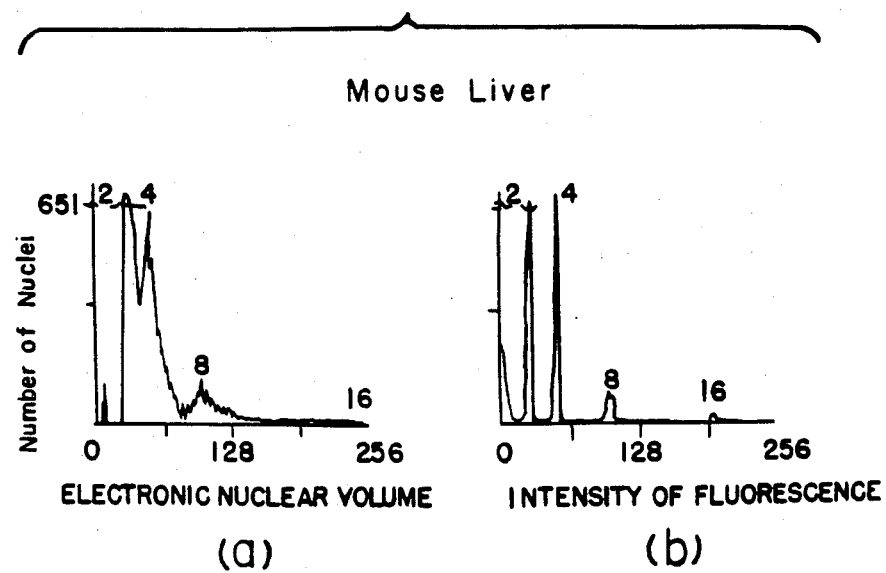
FIGS. 30(a) and 30(b) are electronic nuclear volume and intensity of fluorescence histograms for CF1 mouse liver nuclei.
Figure 31:
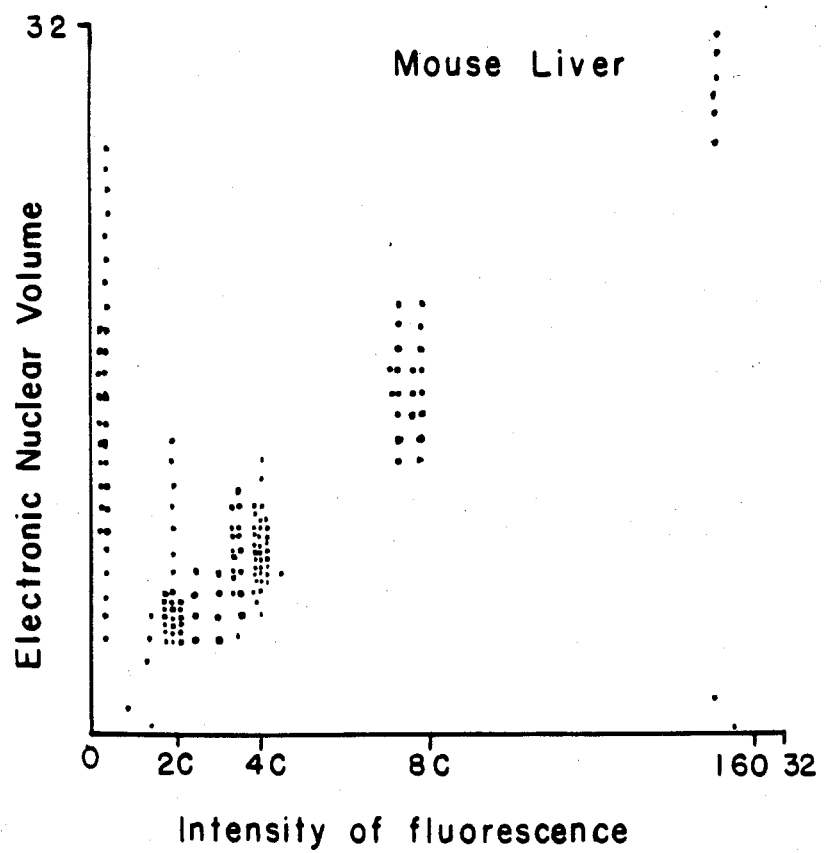
FIG. 31 is a combined plot of electronic nuclear volume and DNA fluorescence of CF1 mouse liver nuclei.

Examples of combined electronic nuclear volume (as differentiated from cell volume) and DNA fluorescence are illustrated in FIGS. 28, 29 and 31. Again, these samples were prepared using the same nuclear isolation medium and dye as the samples for FIGS. 22-26.

In FIGS. 30(a) and 30(b), 256 channel single parameter data of CF1 mouse liver nuclei by electronic nuclear volume and DNA fluorescence is shown. These data illustrate the application of the transducer of the present invention in the simultaneous analysis of a variety of samples utilizing fluorescent and electronic impedance measurements.

Figure 32:
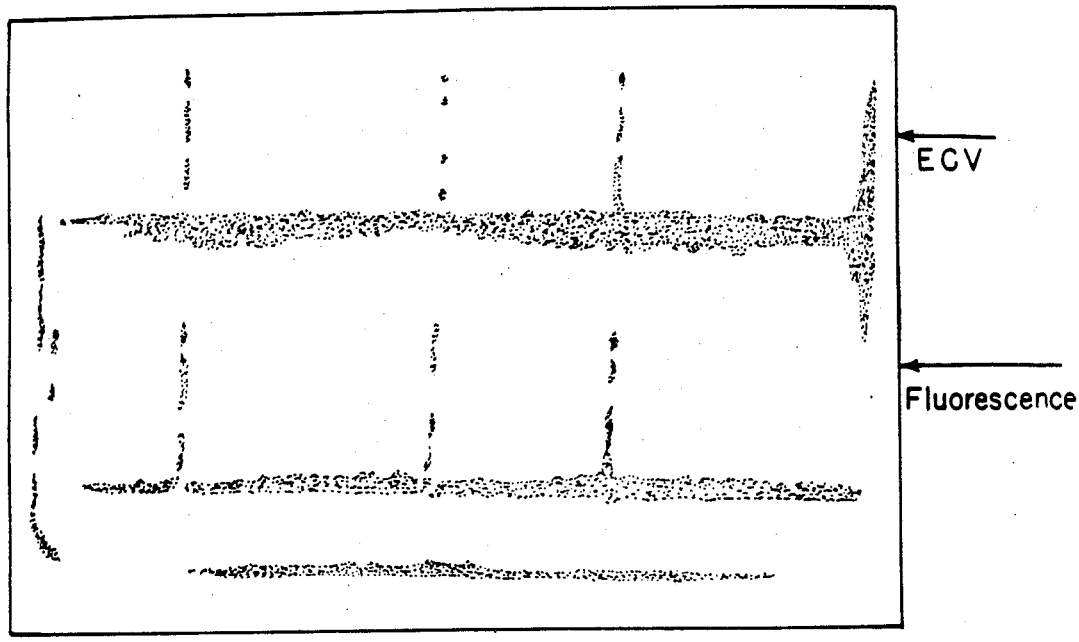
FIGS. 32 and 33 are reproductions of actual oscilloscope tracings for simultaneous electronic nuclear volume and fluorescence pulses for mouse liver nuclei.
Figure 33:
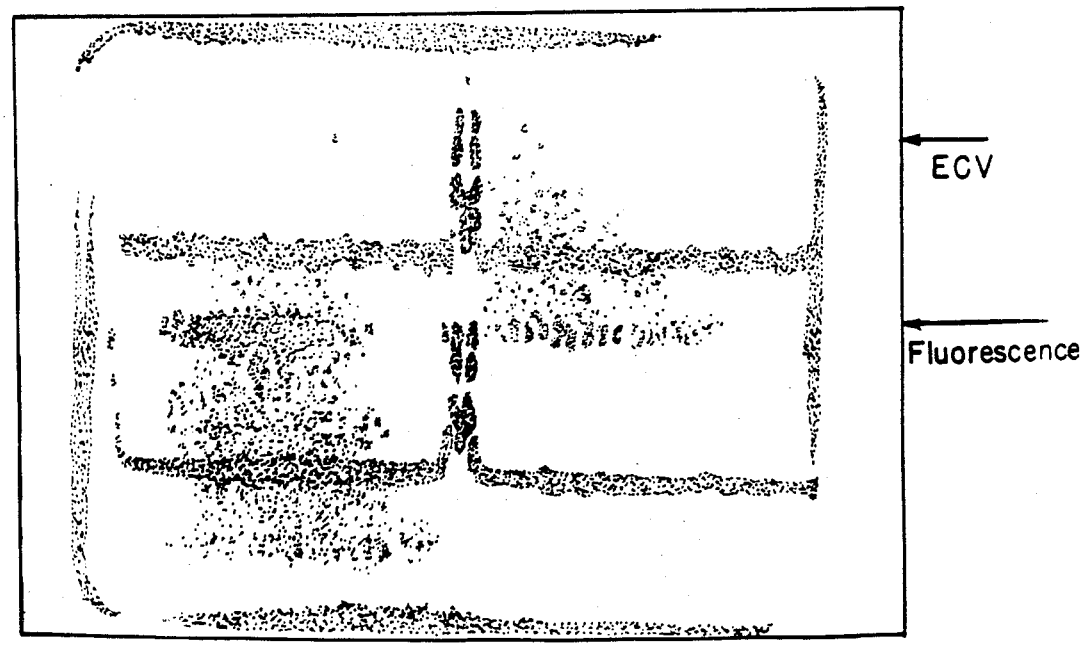

FIGS. 31 and 32 further illustrate the simultaneous nature of the electronic nuclear volume and DNA fluorescence measurements possible with the transducer of this invention. FIGS. 31 and 32 are reproductions of dual channel oscilloscope tracings of electronic and optical measurements on mouse liver. Again, the mouse liver tissue samples were prepared using the same nuclear isolation medium and dye as the previous examples, and the optical measurements were of fluorescence. As can be seen from these Figures, the transducer of the present invention truly results in simultaneous electronic volume and optical measurements.

Although various aspects of the present invention has been described and illustrated with reference to exemplary embodiments, it is not meant to limit the invention to these specific embodiments. Various modifications are possible, and within the skill of those working in this art, without departing from the true spirit and scope of the invention.

What is claimed is:

1. A flow transducer comprising means defining an aperture having an axis, said aperture having at least one flat side, means defining an inlet chamber and an outlet chamber immediately adjacent the aperture along its axis, at least one of said inlet and outlet chamber having walls disposed at an angle of at least 5° relative to the plane of the aperture, said at least one of said inlet and outlet chambers at a distance from the aperture of twice the width of the aperture in a plane through its axis having a cross-section area at least 10 times the cross-sectional area of said aperture.

2. A transducer for a flow cytometer in accordance with claim 1 wherein said transducer is formed of a plurality of solid polygons joined such that adjacent flat surfaces of said polygons define walls of the aperture for the flow cytometer, and others of the surfaces of said polygons define said at least one of said inlet and outlet chambers.

3. A flow cytometer for making simultaneous electronic and optical measurements on a particle flowing through a sensing zone thereof, comprising a transducer formed of a plurality of solid polygons joined such that adjacent flat surfaces of said polygons define a polygonal aperture at the sensing zone and other surfaces of said polygons define inlet and outlet chambers to said aperture, at least one of said inlet and outlet chambers having a predefined geometric relation to said aperture, said inlet and outlet chambers defining an arch shaped fluid passageway with the aperture at the arch vertex, means for establishing a flow of electrolyte through said aperture, said inlet and outlet chambers being configured to establish laminar flow of said electrolyte through said aperture, injector means for injecting samples of particles into said laminar flow of electrolyte, one or more electrodes coupled to said inlet chamber and one or more electrodes coupled to said outlet chamber, means for establishing a current flow through said aperture between said electrodes, monitoring means for monitoring the electrical current flow through said aperture, at least one of the solid polygons defining said aperture being an element in an optical measurement system, said system including means for introducing exciting light through said at least one solid polygon into said aperture, and means for collecting light from a sample particle in said aperture.

4. A flow cytometer in accordance with claim 3 wherein the predetermined geometric relation between said at least one of the inlet and outlet chambers and the aperture is such that walls of said at least one of the inlet and outlet chambers join the aperture at an angle equal to at least 5° with respect to the plane of the aperture, and in which at a distance in the said at least one of inlet and outlet chambers from the aperture equal to twice the width of the aperture along any plane through its axis, the cross-sectional area of said at least one of the inlet and outlet chambers being at least ten times the cross-sectional area of the aperture.

5. A flow cytometer for making simultaneous electronic and optical measurements on a particle flowing through a sensing zone thereof, comprising a transducer formed of a plurality of solid polygons joined such that adjacent surfaces of said polygons define an aperture at the sensing zone and other surfaces of said polygons define inlet and outlet chambers to said aperture at least one of said inlet and outlet chambers having a predefined geometric relation to said aperture, said inlet and outlet chambers defining an arch shaped fluid passageway with the aperture at the arch vertex, means for establishing a flow of electrolyte through said aperture, said inlet and outlet chambers being configured to establish laminar flow of said electrolyte through said aperture, injector means for injecting samples of particles into said laminar flow of electrolyte, one or more electrodes coupled to said inlet chamber and one or more electrodes coupled to said outlet chamber, means for establishing a current flow through said aperture between said electrodes, monitoring means for monitoring the electrical current flow through said aperture, at least one of the solid polygons defining said aperture being an element in an optical measurement system, said system including means for introducing exciting light through at least one solid polygon into said aperture, and means for collecting light from a sample particle in said aperture.

6. A flow transducer comprising means defining an aperture having an axis, means defining an inlet chamber and an outlet chamber immediately adjacent the aperture along its axis at least one of said inlet and outlet chambers having walls disposed at an angle of at least 5° relative to the plane of the aperture, said at least one of said inlet and outlet chambers at a distance from the aperture of twice the width of the aperture in a plane through its axis having a cross-sectional area which is rotationally asymmetric with respect to the axis of the aperture and which is at least 10 times the cross-sectional area of said aperture.

* * * * *

UNITED STATES PATENT AND TRADEMARK OFFICE
CERTIFICATE OF CORRECTION

PATENT NO. : 4,818,103

DATED : April 4, 1989

INVENTOR(S) : Richard A. Thomas and Ross W. Eggleston

It is certified that error appears in the above-identified patent and that said Letters Patent is hereby corrected as shown below:

On the title page, item [75],
    Delete the name of Jerry T. Thornthwaite as an inventor..

On the title page, insert the following Disclaimer Notice:

--The term of this patent subsequent to June 16, 2004, has been disclaimed.--

Signed and Sealed this

Ninth Day of January, 1990

*Attest:*

JEFFREY M. SAMUELS

*Attesting Officer*     *Acting Commissioner of Patents and Trademarks*